United States Patent
Kang et al.

(10) Patent No.: US 9,901,318 B2
(45) Date of Patent: Feb. 27, 2018

(54) X-RAY DETECTION PANEL, X-RAY IMAGING APPARATUS, AND X-RAY IMAGE GENERATION METHOD

(71) Applicant: Samsung Electronics Co., Ltd., Suwon-si (KR)

(72) Inventors: Dong-Goo Kang, Suwon-si (KR); Sung-Hoon Kang, Suwon-si (KR); Sang-Wook Han, Busan (KR); Young-Hun Sung, Hwaseong-si (KR); Hyun-Hwa Oh, Hwaseong-si (KR)

(73) Assignee: Samsung Electronics Co., Ltd., Suwon-si (KR)

(*) Notice: Subject to any disclaimer, the term of this patent is extended or adjusted under 35 U.S.C. 154(b) by 165 days.

(21) Appl. No.: 14/142,140

(22) Filed: Dec. 27, 2013

(65) Prior Publication Data

US 2014/0185765 A1 Jul. 3, 2014

(30) Foreign Application Priority Data

Dec. 27, 2012 (KR) .................. 10-2012-0154937

(51) Int. Cl.
*A61B 6/00* (2006.01)
*A61B 6/04* (2006.01)
(Continued)

(52) U.S. Cl.
CPC ............ *A61B 6/482* (2013.01); *A61B 6/4208* (2013.01); *A61B 6/4233* (2013.01); *A61B 6/502* (2013.01);
(Continued)

(58) Field of Classification Search
CPC ..... A61B 6/4208; A61B 6/4233; A61B 6/482; A61B 6/502; G01T 1/2018
(Continued)

(56) References Cited

U.S. PATENT DOCUMENTS 4,029,963 A 6/1977 Alvarez et al.
4,484,340 A * 11/1984 Yamaguchi ............ G01T 1/185
378/19

(Continued)

FOREIGN PATENT DOCUMENTS

JP 6-225868 A 8/1994
KR 10-2010-0040652 A 4/2010
KR 10-2012-0011692 A 2/2012

OTHER PUBLICATIONS

Extended European Search Report dated Jun. 1, 2017, in corresponding European Application No. 13192797.2 (8 pages in English).

*Primary Examiner* — Allen C. Ho
(74) *Attorney, Agent, or Firm* — NSIP Law

(57) ABSTRACT

An X-ray imaging apparatus includes an X-ray generator configured to emit X-rays to a subject; an X-ray detection panel including a plurality of light receiving elements each configured to receive X-rays that have passed through the subject, convert the X-rays into an electric signal, and output the electric signal, and a plurality of capacitor modules respectively corresponding to the plurality of light receiving elements, each of the plurality of capacitor modules including a plurality of capacitors connected to a corresponding one of the light receiving elements and configured to store the electric signal output from the corresponding light receiving element in at least one capacitor of the plurality of capacitors; and an image processor configured to read out the electric signal stored in the at least one capacitor of each of the plurality of capacitor modules to generate at least one X-ray image.

22 Claims, 13 Drawing Sheets

(51) Int. Cl.
*G01T 1/20* (2006.01)
*G01T 1/24* (2006.01)
*G01N 23/04* (2018.01)
*G01T 1/16* (2006.01)
*G01T 1/17* (2006.01)
*G01T 1/29* (2006.01)

(52) U.S. Cl.
CPC .............. *G01N 23/04* (2013.01); *G01T 1/16* (2013.01); *G01T 1/17* (2013.01); *G01T 1/2018* (2013.01); *G01T 1/2985* (2013.01)

(58) Field of Classification Search
USPC .......... 378/37, 98.8, 98.9, 98.11; 250/370.09
See application file for complete search history.

(56) References Cited

U.S. PATENT DOCUMENTS

| | | | | |
|---|---|---|---|---|
| 5,253,282 A * | 10/1993 | Pelc | ..................... | A61B 6/4035 378/62 |
| 5,570,403 A * | 10/1996 | Yamazaki | ............. | A61B 6/032 378/19 |
| 5,629,524 A * | 5/1997 | Stettner | ................ | G01T 1/2018 250/370.09 |
| 5,661,774 A * | 8/1997 | Gordon | ............... | G01N 23/046 378/101 |
| 5,943,388 A * | 8/1999 | Tümer | ................. | G01V 5/0041 378/98.11 |
| 5,949,811 A * | 9/1999 | Baba | .................... | A61B 6/4225 378/108 |
| 6,173,034 B1 * | 1/2001 | Chao | ..................... | A61B 6/482 378/37 |
| 6,362,482 B1 * | 3/2002 | Stettner | ................ | G01T 1/1644 250/370.01 |
| 6,683,934 B1 * | 1/2004 | Zhao | ..................... | A61B 6/032 378/37 |
| 6,904,126 B2 * | 6/2005 | Endo | ..................... | A61B 6/583 250/370.09 |
| 6,922,462 B2 * | 7/2005 | Acharya | ................ | A61B 6/405 378/98.11 |
| 6,952,464 B2 * | 10/2005 | Endo | ..................... | G01T 1/2928 250/370.09 |
| 7,031,425 B2 * | 4/2006 | Hsieh | .................... | A61B 6/022 378/5 |
| 7,127,031 B2 * | 10/2006 | Endo | ..................... | A61B 6/405 257/E27.132 |
| 7,170,041 B2 * | 1/2007 | Rahn | ..................... | H04N 3/155 250/208.1 |
| 7,187,756 B2 | 3/2007 | Gohno et al. | | |
| 7,227,926 B2 * | 6/2007 | Kameshima | ........... | A61B 6/405 378/98.8 |
| 7,283,609 B2 * | 10/2007 | Possin | ................... | G01T 1/2018 250/370.09 |
| 7,310,404 B2 * | 12/2007 | Tashiro | .................. | A61B 6/032 378/10 |
| 7,386,089 B2 * | 6/2008 | Endo | ..................... | A61B 6/482 378/114 |
| 7,573,037 B1 * | 8/2009 | Kameshima | ............. | A61B 6/00 250/370.09 |
| 7,711,082 B2 * | 5/2010 | Fujimoto | ............... | A61B 6/032 378/115 |
| 7,787,590 B2 * | 8/2010 | Okamura | ................. | A61B 6/00 378/62 |
| 7,812,314 B1 * | 10/2010 | Smith | ...................... | G01T 7/00 250/370.09 |
| 7,813,474 B2 * | 10/2010 | Wu | ........................ | A61B 6/032 378/16 |
| 7,826,587 B1 * | 11/2010 | Langan | .................. | A61B 6/032 378/16 |
| 7,829,860 B2 * | 11/2010 | Nygard | ................. | G01T 1/2018 250/366 |
| 7,949,088 B2 * | 5/2011 | Nishide | .................. | A61B 6/032 378/16 |
| 8,159,286 B2 * | 4/2012 | Rao | ...................... | G01T 1/2985 327/337 |
| 8,199,875 B2 * | 6/2012 | Chandra | ................ | A61B 6/032 378/16 |
| 8,311,182 B2 * | 11/2012 | Chandra | ................ | A61B 6/03 378/5 |
| 8,422,636 B2 * | 4/2013 | Greenberg | ................ | G01T 1/29 378/207 |
| 8,447,011 B2 * | 5/2013 | Ohta | ........................ | A61B 6/00 378/62 |
| 8,483,360 B2 * | 7/2013 | Litvin | .................... | A61B 6/032 378/4 |
| 8,525,122 B2 * | 9/2013 | Chappo | .................... | A61B 6/00 250/370.11 |
| 8,798,352 B2 * | 8/2014 | Miyamoto | ............... | A61B 6/00 382/132 |
| 8,837,801 B2 * | 9/2014 | Jang | ......................... | A61B 6/00 382/132 |
| 9,014,455 B2 * | 4/2015 | Oh | .......................... | A61B 6/52 378/98.11 |
| 9,149,241 B2 * | 10/2015 | Kim | ....................... | A61B 6/482 |
| 9,274,235 B2 * | 3/2016 | Kang | ..................... | G01N 23/04 |
| 9,325,913 B2 * | 4/2016 | Wei | ......................... | G01T 1/24 |
| 9,348,035 B2 * | 5/2016 | Liu | ................... | H01L 27/14607 |
| 9,354,331 B2 * | 5/2016 | Sagoh | .................... | A61B 6/032 |
| 9,417,339 B2 * | 8/2016 | Spahn | ..................... | G01T 1/247 |
| 9,504,439 B2 * | 11/2016 | Yi | ......................... | A61B 6/5205 |
| 9,532,759 B2 * | 1/2017 | Taguchi | ................... | A61B 6/032 |
| 9,541,655 B2 * | 1/2017 | Sonoda | .................. | G01T 1/2018 |
| 9,595,101 B2 * | 3/2017 | Kato | ........................ | G06T 11/005 |
| 9,597,052 B2 * | 3/2017 | Lee | ........................ | A61B 6/563 |
| 9,689,996 B2 * | 6/2017 | Rao | ................... | H01L 27/14661 |

\* cited by examiner

X-RAY DETECTION PANEL, X-RAY IMAGING APPARATUS, AND X-RAY IMAGE GENERATION METHOD

CROSS-REFERENCE TO RELATED APPLICATIONS

This application claims the benefit of Korean Patent Application No. 10-2012-0154937 filed on Dec. 27, 2012 in the Korean Intellectual Property Office, the disclosure of which is incorporated herein by reference in its entirety for all purposes.

BACKGROUND

1. Field

This application relates to an X-ray detection panel, an X-ray imaging apparatus using the X-ray detection panel, and an X-ray image generation method using the X-ray detection panel.

2. Description of Related Art

An X-ray imaging apparatus is an imaging system that acquires an image of tissues inside a subject by emitting X-rays (also referred to as Roentgen rays) to the subject, such as a human body or an object. Examples of the X-ray imaging apparatus include a Computed Tomography (CT) or Full Field Digital Mammography (FFDM) apparatus. In the X-ray imaging apparatus, X-rays emitted to the subject may be transmitted or absorbed by a material of the subject according to properties of the material. The X-ray imaging apparatus is used to detect diseases or other abnormalities of a human body, or to observe internal structures of objects or components, and may also be used as a scanner to scan luggage in the airport, among other uses Considering the operation principle of the X-ray imaging apparatus, after X-rays are emitted to a subject, such as a human body, and the X-ray imaging apparatus receives X-rays that have passed through or around the subject, the X-ray imaging apparatus converts the received X-rays into electric signals, reads out the electric signals to generate an X-ray image, and then displays the X-ray image to a user.

An FFDM apparatus is a medical imaging apparatus that captures an image of a female breast and detects defects, such as cancer tissues. Through use of the FFDM apparatus, efficiency of inspection of diseases, such as breast cancer, etc., is increased, and diagnosis of a greater number of cases than can be diagnosed using conventional film type mammography may be possible.

The FFDM apparatus acquires an X-ray image of a breast by emitting X-rays to the breast and receiving X-rays that have passed through the breast. More specifically, the breast is placed on a flat support plate provided with a detector, and is compressed using a compressor to increase an X-ray irradiation area. Then, an X-ray generator located above the support plate emits X-rays to the breast compressed by the compressor, and finally, a planar X-ray image that shows tissues inside the breast is obtained from the detector.

SUMMARY

In one general aspect, an X-ray imaging apparatus includes an X-ray generator configured to emit X-rays to a subject; an X-ray detection panel including a plurality of light receiving elements each configured to receive X-rays that have passed through the subject, convert the X-rays into an electric signal, and output the electric signal, and a plurality of capacitor modules respectively corresponding to the plurality of light receiving elements, each of the plurality of capacitor modules including a plurality of capacitors connected to a corresponding one of the light receiving elements and configured to store the electric signal output from the corresponding light receiving element in at least one capacitor of the plurality of capacitors; and an image processor configured to read out the electric signal stored in the at least one capacitor of each of the plurality of capacitor modules to generate at least one X-ray image.

Each capacitor of the plurality of capacitors may be further configured to be electrically connected to or disconnected from the corresponding light receiving element according to an X-ray energy level of the X-rays emitted from the X-ray generator, and store the electric signal output from the corresponding light receiving element in response to the corresponding light receiving element receiving X-rays while the capacitor is electrically connected to the corresponding light receiving element.

The apparatus may further include a plurality of switching unit units respectively corresponding to the plurality of light receiving elements, each of the switching units being configured to select at least one capacitor of the plurality of capacitors connected to the corresponding light receiving element according to an X-ray energy level of the X-rays emitted from the X-ray generator to enable the selected at least one capacitor to store the electric signal output from the corresponding light receiving element.

Each of the switching units may be further configured to select a plurality of capacitors of the plurality of capacitors connected to the corresponding light receiving element according to a plurality of X-ray energy levels of the X-rays emitted from the X-ray generator to enable the selected capacitors to respectively store electric signals respectively corresponding to the plurality of X-ray energy levels output from the corresponding light receiving element; and the image processor may be further configured to read out the electric signals respectively corresponding to the plurality of X-ray energy levels stored in the selected capacitors of the plurality of capacitor modules according to the plurality of X-ray energy levels to generate a plurality of X-ray images respectively corresponding to the plurality of X-ray energy levels.

The X-ray generator may be further configured to emit X-rays having a plurality of X-ray energy levels to the subject by emitting the X-rays to the subject a plurality of times with a different X-ray energy level each of the plurality of times the X-rays are emitted to the subject; each of the plurality of light receiving elements may be further configured to output the electric signal a plurality of times in response to receiving, a plurality of times, the X-rays that have passed through the subject; and the plurality of capacitors of each of the capacitor modules may be further configured to store the electric signal output from the corresponding light receiving element in a different one of the plurality of capacitors according to an X-ray energy level of the X-rays emitted to the subject each of the plurality of times the X-rays are emitted to the subject.

The image processor may be further configured to read out electric signals corresponding to a same X-ray energy level from the plurality of capacitors of the plurality of capacitor modules.

Each of the light receiving elements may include a scintillator configured to receive the X-rays that have passed through the subject, and generate light in response to the X-rays; and a photodiode configured to sense the light generated by the scintillator, and output the electric signal in response to the light.

The X-ray detection panel may further include a wafer including the plurality of light receiving elements, and a wiring layer including the plurality of capacitor modules; and the X-ray detection panel may be a front-side illumination type X-ray detection panel in which the wiring layer is disposed between the scintillator and the wafer, and the X-ray detection panel is configured to receive the X-rays that have passed through the subject on a surface of the scintillator facing away from the wiring layer; or the X-ray detection panel may be a back-side illumination type X-ray detection panel in which the wafer is disposed between the scintillator and the wiring layer, and the X-ray detection panel is configured to receive the X-rays that have passed through the subject on a surface of the scintillator facing away from the wafer.

In another general aspect, an X-ray detection panel includes a light receiving element configured to receive X-rays, convert the X-rays into an electric signal, and output the electric signal; and a plurality of storage elements connected to the light receiving element and configured to selectively store the electric signal output from the light receiving element.

Each of the storage elements may be further configured to be electrically connected to or disconnected from the light receiving element according to an X-ray energy level, and store the electric signal output from the light receiving element in response to the light receiving element receiving X-rays while the storage element is electrically connected to the light receiving element.

The X-rays received by the light receiving element may correspond to an X-ray energy level; and the X-ray detection panel may further include a switching unit configured to select any one storage element of the plurality of storage elements connected to the light receiving element according to the X-ray energy level, and electrically connect the selected storage element to the light receiving element to enable the selected storage element to store the electric signal output from the light receiving elements so that the stored electric signal corresponds to the X-ray energy level.

The plurality of storage elements may be further configured to selectively store the electric signal output from the light receiving element in a different one of the plurality of storage elements each of a plurality of times the light receiving element receives X-rays.

The X-ray detection panel may be configured to operate in conjunction with an image processor configured to read out the electric signals stored in the plurality of storage elements to generate a plurality of X-ray images after the light receiving element has received X-rays a plurality of times.

The X-rays received by the light receiving element a plurality of times may respectively correspond to a plurality of different X-ray energy levels; and the image processor may be further configured to read out the electric signals stored in the plurality of storage elements according to an X-ray energy level so that the plurality of X-ray images respectively correspond to the plurality of different X-ray energy levels.

The light receiving element may include a scintillator configured to receive the X-rays, and generate light in response to the X-rays; and a complementary metal-oxide-semiconductor (CMOS) chip including a photodiode configured to sense the light generated by the scintillator, and output an electric signal in response to the light generated by the scintillator.

The X-ray detection panel may further include a wiring layer including the plurality of storage elements; and the X-ray detection panel may be a back-side illumination type X-ray detection panel in which the CMOS chip is disposed between the scintillator and the wiring layer, and the X-ray detection panel is configured to receive the X-rays on a surface of the scintillator facing away from the CMOS chip.

In another general aspect, an X-ray image generation method includes selecting, for each of a plurality of capacitor modules each including a plurality of capacitors, one capacitor of the plurality of capacitors according to an X-ray energy level of X-rays to be emitted from an X-ray generator; emitting X-rays having the X-ray energy level from the X-ray generator to a subject; receiving X-rays that have passed through the subject with each of a plurality of light receiving elements respectively corresponding to the plurality of capacitor modules, each of the plurality of light receiving elements converting the X-rays to an electric signal and outputting the electric signal; and storing, for each of the plurality of capacitor modules, the electric signal output from a corresponding one of the plurality of light receiving elements in the selected capacitor.

The method may further include reading out the electric signal stored in the selected capacitor of each of the plurality of capacitor modules to generate an X-ray image.

The method may further include repeating the selecting, the emitting, the receiving, and the storing for each of a plurality of different X-ray energy levels of the X-rays to be emitted from the X-ray generator to store different electric signals respectively corresponding to the different X-ray energy levels in the selected capacitors of each of the plurality of capacitor modules.

The method may further include reading out the stored different electric signals respectively corresponding to the different X-ray energy levels to generate a plurality of X-ray images respectively corresponding to the different X-ray energy levels.

Other features and aspects will be apparent from the following detailed description, the drawings, and the claims.

DETAILED DESCRIPTION

Figure 1:
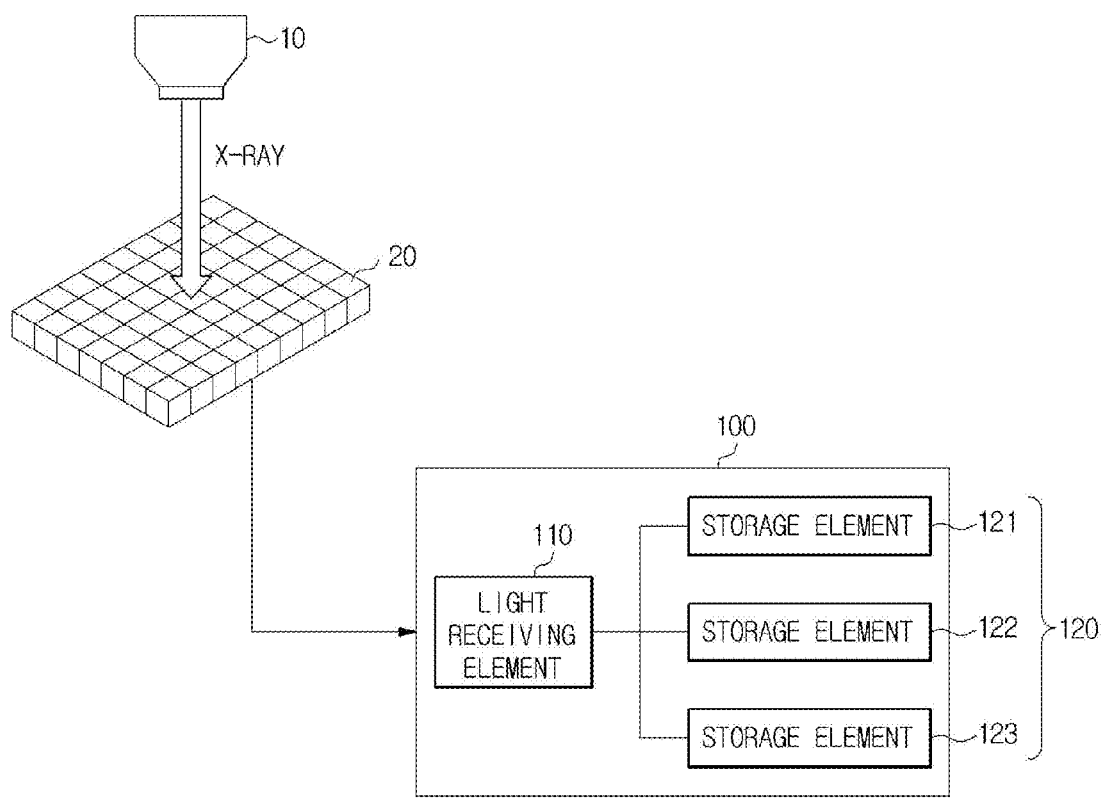
FIG. 1 is a diagram illustrating an example of an X-ray imaging apparatus.

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, description of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

An X-ray detection panel and an X-ray imaging apparatus are described below with reference to FIGS. 1 to 6.

FIG. 1 is a diagram illustrating an example of an X-ray imaging apparatus. In the example illustrated in FIG. 1, the X-ray imaging apparatus includes an X-ray generator 10 located on one side of a subject (not shown) that generates and emits X-rays to the subject, and an X-ray detection panel 20 located on the other side of the subject to receive X-rays emitted from the X-ray generator 10. The X-ray detection panel 20 receives X-rays that have passed through or around the subject, converts the received X-rays into electric signals, and stores the electric signals.

The X-ray generator 10 may include an X-ray tube that generates X-rays having an energy level corresponding to a voltage applied thereto, and an electric circuit that adjusts a voltage to apply a predetermined voltage to the X-ray tube. In the X-ray tube, as a speed of electrons accelerated by the predetermined voltage applied to the X-ray tube is reduced near an atomic nucleus by the Coulomb force, X-rays of various energy levels are emitted due to energy conservation. In other words, the X-ray generator 10 may generate X-rays of various energy levels according to a voltage applied thereto and emit the X-rays to the subject.

The X-ray detection panel 20 functions to receive X-rays and output and store electric signals corresponding to the X-rays. For example, the X-ray detection panel 20 may include a flat panel detector.

The X-ray detection panel 20 is described in greater detail below.

Referring to FIG. 1, the X-ray detection panel includes a plurality of light receiving modules 100.

Each of the plurality of light receiving modules 100 constituting the X-ray detection panel 20 includes a light receiving element 110 that receives X-rays that have passed through the subject, converts the X-rays into an electric signal, and outputs the electric signal, and a storage element module 120 that is electrically connected to the light receiving element 110 to store the electric signal output from the light receiving element 110.

One light receiving element 110 of any one light receiving module 100 may be electrically connected to at least two storage elements, for example, three storage elements 121 to 123 as illustrated in FIG. 1.

In other words, a plurality of storage elements 121 to 123 may be allotted to one light receiving element 110 of the X-ray detection panel 20 included in the X-ray imaging apparatus, and the respective storage elements 121 to 123 may individually store electric signals output from the light receiving element 110.

In greater detail, one light receiving element 110 of each light receiving module 100 may be connected to the plurality of storage elements 121 to 123, and the respective storage elements 121 to 123 may be electrically connected to or disconnected from the light receiving element 110 as necessary.

More specifically, before the light receiving element 110 outputs an electric signal corresponding to X-rays having a predetermined energy level, any one storage element, e.g., the storage element 121, among the plurality of storage elements 121 to 123 is selected. The selected storage element 121 is electrically connected to the light receiving element 110, and the other storage elements 122 and 123 that are not selected are electrically disconnected from the light receiving element 110. Therefore, only the selected storage element 121 stores the electric signal output from the light receiving element 110.

Accordingly, if one light receiving element 110 outputs a plurality of electric signals, the electric signals may be stored in different ones of the storage elements 121 to 123. Therefore, if X-rays are emitted a plurality of times, a plurality of electric signals respectively corresponding to different X-ray emission times may be stored in different ones of the storage elements 121 to 123.

Hereinafter, a group of the plurality of storage elements 121 to 123 connected to one light receiving element 110 will be referred to as a storage element module 120. In addition, if the storage elements 121 to 123 are capacitors, the storage element module 120 will be referred to as a capacitor module 120.

The X-ray imaging apparatus is described in greater detail below with reference to FIGS. 2 to 6.

Figure 2:
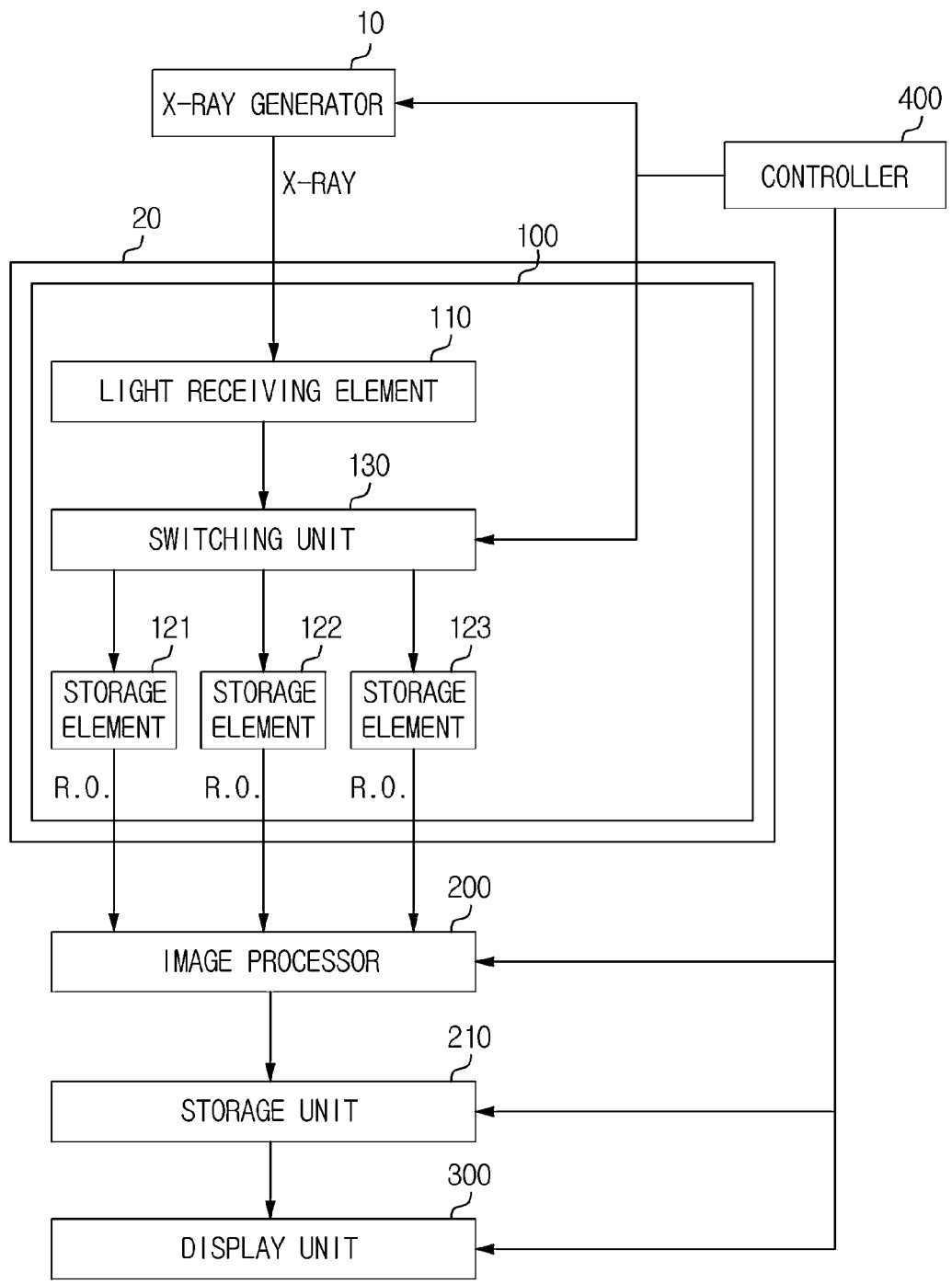
FIG. 2 is a diagram illustrating an example of an overall configuration of the X-ray imaging apparatus.

FIG. 2 is a diagram illustrating an example of an overall configuration of the X-ray imaging apparatus. As illustrated in FIG. 2, the X-ray imaging apparatus includes the X-ray generator 10, the X-ray detection panel 20, an image processor 200, a storage unit 210, a display unit 300, and a controller 400.

The X-ray generator 10 of the X-ray imaging apparatus generates and emits X-rays to the subject as described above. X-rays may be emitted a plurality of times, and X-rays emitted at the different times may have different energy levels. Of course, as necessary, all or some of X-rays emitted at the respective times may have the same energy level. The X-rays, emitted from the X-ray generator 10 and having passed through the subject, are received by the X-ray detection panel 20.

The X-ray detection panel 20 generates and stores electric signals upon receiving X-rays that have passed through the subject. As necessary, the X-ray detection panel 20 may include a support frame to mount the X-ray detection panel 20, and a protective cover to protect the X-ray detection panel 20.

Figure 3:
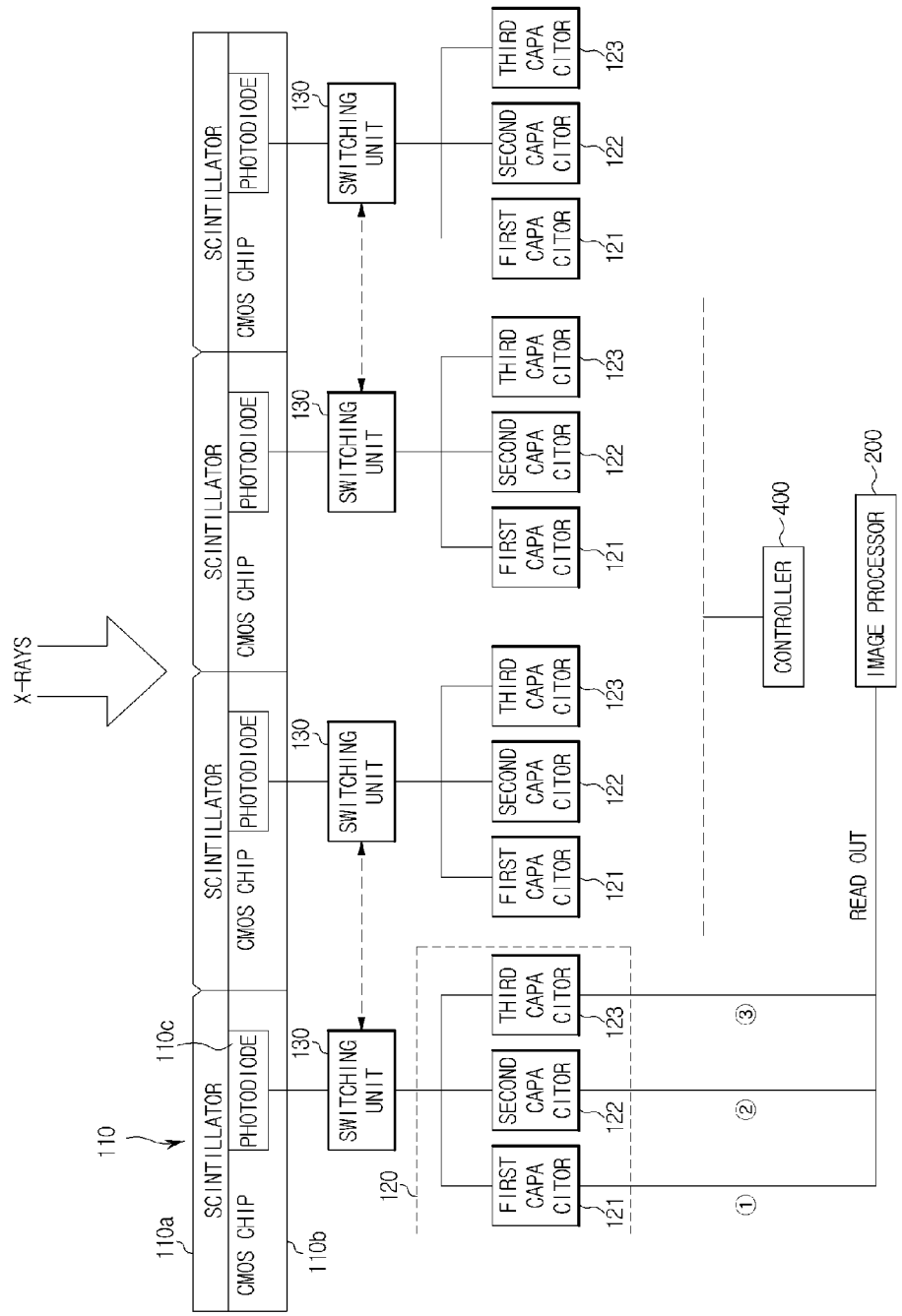
FIG. 3 is a diagram illustrating an example of an overall configuration of an X-ray detection panel.

FIG. 3 is a diagram illustrating an example of an overall configuration of the X-ray detection panel 20. As illustrated in FIGS. 2 and 3, the X-ray detection panel 20 includes the light receiving element 110 that receives X-rays, converts the received X-rays into electric signals, and outputs the electric signals, the plurality of storage elements 121 to 123 that store the electric signals output from the light receiving element 110, and a switching unit 130 that functions to select any one storage element among the plurality of storage elements 121 to 123.

As described above, one light receiving element 110 receives X-rays that have passed through the subject and outputs an electric signal.

Referring to FIG. 3, the light receiving element 110 includes a scintillator 110*a* that receives X-rays and outputs photons (more particularly, visible photons, i.e., visible light) according to the received X-rays, and a light processing element that detects light and generates an image corresponding to an electric signal, for example, a complementary metal-oxide-semiconductor (CMOS) chip 110*b*. More specifically, the CMOS chip 110*b* includes a photodiode 110*c* that detects the photons output from the scintillator 110*a* to generate an electric signal.

Examples of a configuration of the light receiving module 100 are described detail below with reference to FIGS. 4 and 5.

Figure 4:
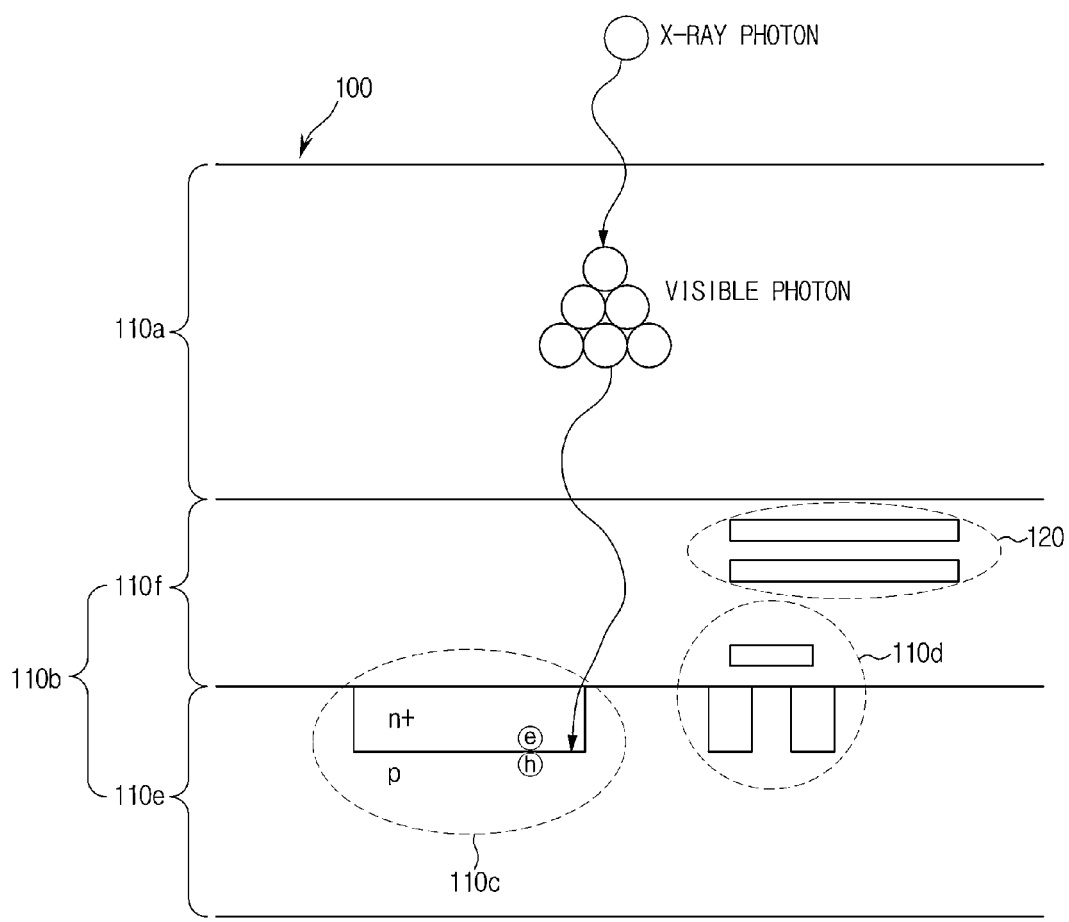
FIG. 4 is a diagram illustrating an example of a light receiving module for explaining how a light receiving converts X-rays into an electric signal.
Figure 5:
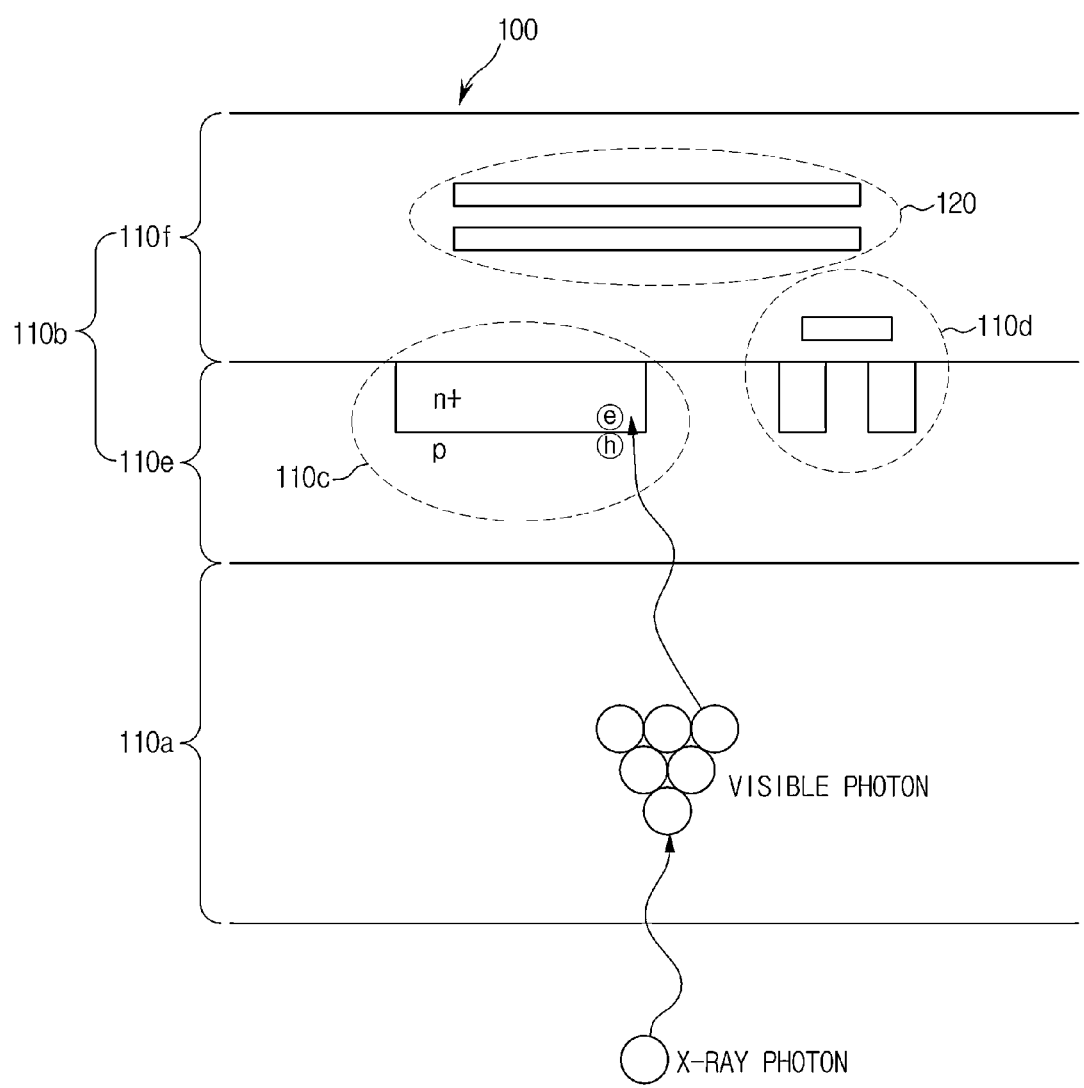
FIG. 5 is a diagram illustrating another example of a light receiving module for explaining how a light receiving element converts X-rays into an electric signal.

FIGS. 4 and 5 are diagrams illustrating different configurations of the light receiving module 100 for explaining how the light receiving element 110 converts X-rays into an electric signal.

The light receiving element 110 may generate an electric signal by collecting light via two methods. One method is a front-side illumination method in which the scintillator 110*a* is arranged on a front surface of the CMOS chip 110*b* to receive X-rays, and the other method is a back-side illumination method in which the scintillator 110*a* is arranged on a back surface of the CMOS chip 110*b* to receive X-rays.

FIG. 4 illustrates an example of front-side illumination, and FIG. 5 illustrates an example of back-side illumination.

In front-side illumination, as illustrated in FIG. 4, the front surface of the CMOS chip 110*b* is used as a light collector. Referring to FIG. 4, in front-side illumination, the scintillator 110*a* is attached to the front surface of the CMOS chip 110*b*. The CMOS chip 110*b* includes a carbon-silicon (C—Si) substrate 110*e*, i.e., a wafer 110*e*, and a wiring layer 110*f*.

The wiring layer 110*f* is formed in an upper portion of the CMOS chip 110*b*, and is attached to the scintillator 110*a*. A variety of circuit elements, for example, the capacitors of the capacitor module 120, are arranged in the wiring layer 110*f*. The wiring layer 110*f* may have a thickness, for example, of about 4~5 μm.

The wafer 110*e*, as illustrated in FIG. 4, is located under the wiring layer 110*f*. The photodiode 110*c* to receive visible light and convert the visible light into an electric signal is arranged in the wafer 110*e*. A transistor 110*d* may be arranged in the wafer 110*e* to selectively transmit the electric signal output from the photodiode 110*c* to any one capacitor of the plurality of capacitors 121, 122, 123 of the capacitor module 120. Although not shown in FIG. 4, a plurality of transistors 110*d* may be provided in the wafer 110*e*, one for each of the plurality of capacitors 121, 122, 123 of the capacitor module 120. The plurality of transistors 110*d* may be the switching unit 130 shown in FIGS. 2 and 3.

Additionally, a substrate (not shown) may be attached to a back surface of the wafer 110*e*.

Referring to FIG. 4, when using front-side illumination, when the scintillator 110*a* receives X-rays and outputs visible photons, the visible photons first pass through the wiring layer 110*f* in which the capacitors 121, 122, 123 of the capacitor module 120 are arranged, and thereafter are incident on the photodiode 110*c* in the wafer 110*e* under the wiring layer 110*f*. Accordingly, a physical distance between a light source in the scintillator 110*a* and the photodiode 110*c* is greater than in back-side illumination, which is described below. As a result, the area of each light receiving element 110 may be problematically reduced because part of the area of each light receiving element 110 may be blocked by circuit elements and wiring elements in the wiring layer 110*f*.

In back-side illumination, as illustrated in FIG. 5, the back surface of the CMOS chip is used as a light collector.

Referring to FIG. 5, in back-side illumination, the scintillator 110*a* is attached to a back surface of the CMOS chip 110*b*, i.e., a back surface of the wafer 110*e* of the CMOS chip 110*b*. The photodiode 110*c* to convert visible light into an electric signal and the transistor 110*d* are arranged in the wafer 110*e*. A thickness of the wafer may be less than 10 μm. Although not shown in FIG. 5, a plurality of transistors 110*d* may be provided in the wafer 110*e*, one for each of the plurality of capacitors 121, 122, 123 of the capacitor module 120. The plurality of transistors 110*d* may be the switching unit 130 shown in FIGS. 2 and 3.

A wiring layer 110*f* in which a variety of circuit elements, for example, the capacitors 121, 122, 123 of the capacitor module 120, are arranged, is placed on the front surface of the wafer 110*e*. A separate wafer or glass substrate (not shown) may be placed on a front surface of the wiring layer 110*f* (an upper surface of the CMOS chip 110*b*), i.e., on a surface of the wiring layer 110*f* to which the wafer 110*e* is not attached.

Referring to FIG. 5, when the scintillator 110*a* receives X-rays and outputs visible photons, the visible photons pass directly to wafer 110*e* in which the photodiode 110*c* is arranged without passing through the wiring layer 110*f*, which results in a physical distance between a light source in the scintillator 110*a* and the photodiode 110*c* that is smaller than in the front-side illumination described above. As a result, it may be possible to increase the area of each light receiving element 110 without increasing the size of the CMOS chip 110*b* because no part of the area of each light receiving element 110 is blocked by circuit elements and wiring elements of the wiring layer 110*f*.

Accordingly, as compared to front-side illumination, back-side illumination may increase the area of each light receiving element 110 without changing the size of the CMOS chip 110*b*, which results in improved noise characteristics and a brighter image.

Referring to FIGS. 2 and 3, each light receiving module 100 of the X-ray detection panel 20, as described above, may include the storage element module 120 including the plurality of storage elements 121 to 123, for example, a plurality of capacitors, that may be electrically connected to the light receiving element 110.

The plurality of storage elements 121 to 123 included in the storage element module 120 store electric signals output from the light receiving element 110. As described above, to store an electric signal output from the light receiving element 110, any one of the plurality of storage elements 121 to 123 is selected arbitrarily or according to predetermined conditions. The selected storage element stores the electric signal output from the light receiving element 110 to allow the image processor 200, which is described below, to generate an X-ray image based on the electric signal.

In other words, whenever the X-ray generator 10 emits X-rays, any one of the plurality of storage elements 121 to 123 of the storage element module 120 is selected arbitrarily or according to predetermined conditions, enabling a plurality of electric signals output from the light receiving element 110 to be stored in different ones of the storage elements 121 to 123.

Operation of the above-described storage elements 121 to 123 is described below.

The storage elements 121 to 123 may not simultaneously store a plurality of electric signals output from the light receiving element 110, but may store only one of the plurality of electric signals output from the light receiving element 110 at a time. This is described in greater detail below.

First, when the light receiving element 110 outputs an electric signal, for example, the storage element 121, such as a capacitor, may receive and store the output electric signal. Thereafter, when the light receiving element 110 outputs a new electric signal, the electric signal stored in the storage element 121 is deleted and the new electric signal is stored in the storage element 121. In other words, each storage element 121 temporarily stores the electric signal output from the light receiving element 110 until a new electric signal is stored in the storage element 121.

Assuming that only one storage element 121, 122, or 123 is connected to one light receiving element 110, if X-ray imaging is performed a plurality of times, the light receiving element 110 outputs a new electric signal each time X-ray imaging is performed, and an electric signal stored in the previous X-ray imaging is deleted. Thus, since the previous electric signal is deleted whenever new X-ray imaging is performed, it is necessary to read out an X-ray image from the storage element 121, 122, or 123 prior to performing new X-ray imaging. In other words, to acquire a plurality of X-ray images corresponding to the number of X-ray imaging operations, it is necessary for the image processor 200 to read out an electric signal from the storage element 121, 122, or 123 prior to initiating a new X-ray imaging operation to acquire an X-ray image for the previous X-ray imaging operation.

However, reading out the X-ray image from the storage element 121 may require a great amount of time because it may be necessary for the image processor 200 to read out electric signals from all of the light receiving modules 100 of the X-ray detection panel 20, and thereafter to combine and generate X-ray images based on the readout results.

Therefore, if only one storage element 121 is provided, the image processor 200 may need to generate an X-ray image each time X-ray imaging is performed, and therefore an X-ray imaging duration may be inevitably increased when a plurality of X-ray imaging operations are necessary, for example, in the case of multi-energy X-ray (MEX) imaging. In particular, when imaging a compressed breast, such as in an FFDM apparatus, the compression of the breast may be painful, and the increased X-ray imaging duration may further increase the pain.

However, in the example in FIGS. 2 and 3, since the plurality of storage elements 121 to 123 are connected to one light receiving element 110 and any one of the plurality of storage elements 121 to 123 is selected to store an electric signal output from the light receiving element 110, the number of electric signals that can be stored is increased according to the number of the storage elements. Accordingly, even if X-rays are emitted a plurality of times and a plurality of electric signals generated from X-rays are output, the image processor 200 need not read out an X-ray image each time X-rays are emitted if the number of X-ray emission operations is equal to or less than the number of the storage elements 121 to 123.

In other words, if the number of X-ray emission operations is equal to or less than the number of the storage elements 121 to 123, the electric signals of the storage elements 121 to 123 may be read out after all of X-ray emission operations have been completed. Accordingly, for example, it may be possible to minimize a subject X-ray exposure duration even in the case of multi-energy x-ray (MEX) imaging, which may minimize deterioration of screen quality due to movement of a subject, and may reduce pain due to compression of the breast.

In the example described above, all of the light receiving modules 100 constituting the X-ray detection panel 20 include the plurality of storage elements 121 to 123. However, in another example, only some of the light receiving modules 100 constituting the X-ray detection panel 20 may include the plurality of storage elements 121 to 123, and remaining ones of the light receiving modules 100 may include only one storage element. This may reduce a manufacturing cost. However, in general, to acquire the most accurate image, all of the light receiving modules 100 constituting the X-ray detection panel 20 should include the plurality of storage elements 121 to 123.

To select any one of the plurality of storage elements 121 to 123, the X-ray detection panel 20 may further include the switching unit 130. The switching unit 130 may electrically connect or disconnect the light receiving element 110 to or from the storage elements 121 to 123 according to a control instruction received from the controller 400, which is described below. In particular, selection of any one storage element using the switching unit 130 may be performed when or before X-rays are emitted. The switching unit 130, for example, may include the transistor 110d illustrated in FIGS. 4 and 5.

Electric signals stored in the storage elements 121 to 123 are read out by the image processor 200. As illustrated in FIGS. 2 and 3, the image processor 200 reads out an X-ray image from the electric signals stored in the storage elements 121 to 123 of the X-ray detection panel 20.

The image processor 200 may read out an X-ray image from the respective storage elements 121 to 123 after X-ray imaging is performed a plurality of times, rather than reading out an X-ray image each time electric signals are stored in the storage elements 121 to 123 for X-ray imaging.

The image processor 200 does not indiscriminately read electric signals from all of the plurality of storage elements 121 to 123 allotted to each of a plurality of light receiving elements 110, but, for example, reads out electric signals from only the storage elements 121 that store electric signals acquired according to a predetermined criterion, for example, according to a predetermined X-ray energy level.

In greater detail, referring to FIG. 3, when or before the X-ray generator 10 emits X-rays to the subject, any one storage element (for example, the storage element 121, hereinafter referred to as a first storage element) of the storage element module 120 of each light receiving element 110 is selected. The switching unit 130 may be used to select the one storage element 121.

The selected first storage elements 121 of the light receiving modules 100 store electric signals that correspond to a predetermined X-ray energy level and are output from the light receiving element 110.

Thereafter, when or before the X-ray generator 10 again emits X-rays, another storage element (for example, the storage element 122, hereinafter referred to as a second storage element) is selected. The selected second storage elements 122 of the light receiving modules 100 store electric signals.

Thereafter, when or before the X-ray generator 10 again emits X-rays, another storage element (for example, the storage element 123, hereinafter referred to as a third storage element) is selected. The selected third storage elements 123 of the respective light receiving elements 110 store electric signals.

After the emission of X-rays is completed, electric signals are stored in the first storage element 121, the second storage element 122, and the third storage element of each storage element module 120.

Then, for example, the image processor 200 first reads out a first X-ray image from the first storage elements 121 (O of FIG. 3), then reads out a second X-ray image from the second storage elements 122 (® of FIG. 3), and finally reads out a third X-ray image from the third storage elements 123 (@ of FIG. 3), thereby acquiring a plurality of X-ray images.

In other words, the image processor 200 reads out respective X-ray images from the storage elements 121 to 123 of the storage element modules 120 according to selection in the case of X-ray imaging.

Although electric signals are stored in and read out from all of the storage elements 121 to 123 in the above example, electric signals may be stored in and read out from only any one of the storage elements 121 to 123, or any two of the storage elements 121 to 123.

A process of storing an electric signal output from the light receiving element 110 in a capacitor 121, 122, 123 and reading out the electric signal by the image processor 200 is described in greater detail below with reference to FIG. 6.

Figure 6:
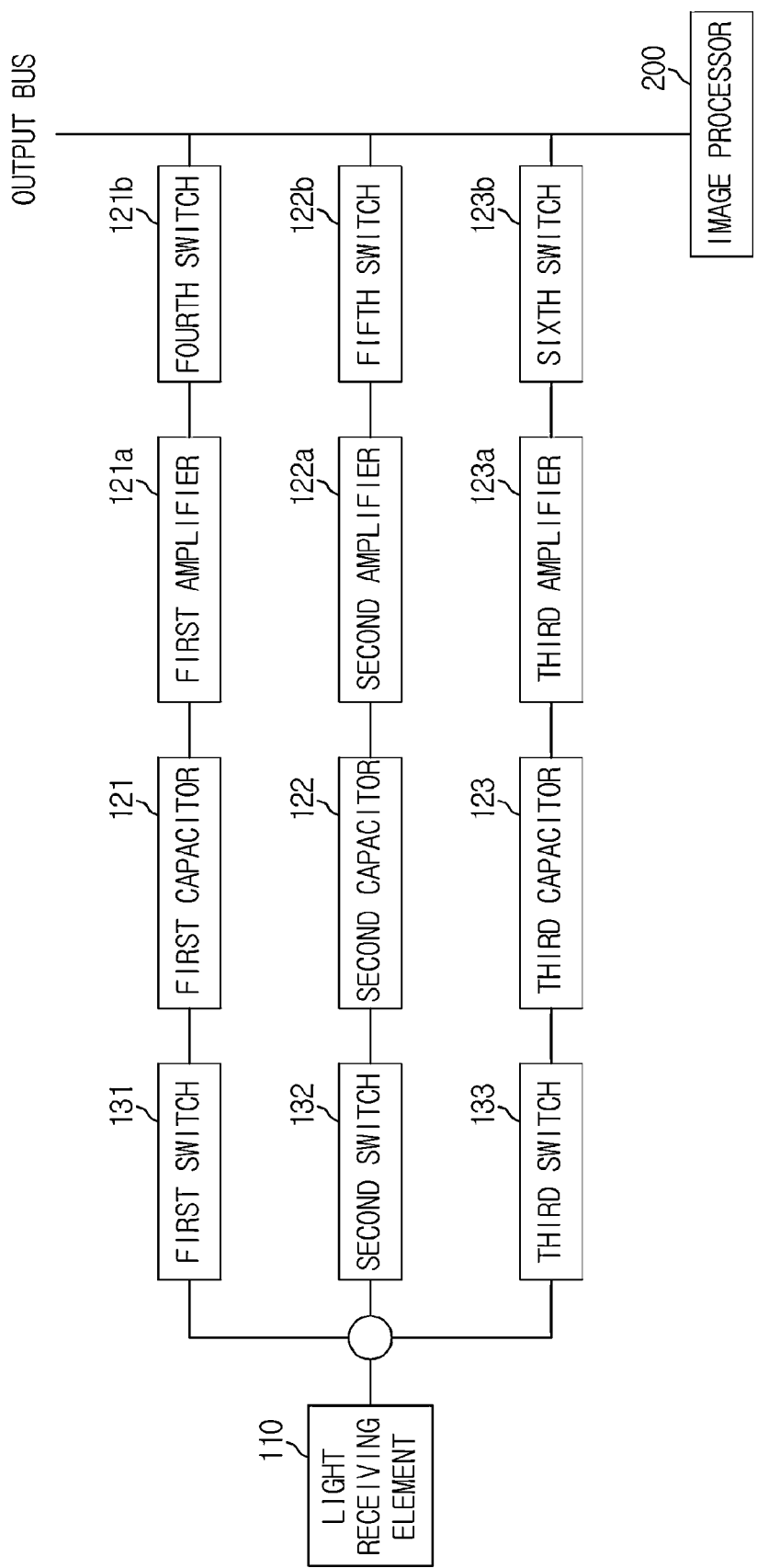
FIG. 6 is a diagram illustrating an example of a configuration to read out an X-ray image from the X-ray detection panel.

FIG. 6 is a diagram illustrating an example of a configuration to read out an X-ray image from the X-ray detection panel 20. In the example illustrated in FIG. 6, the plurality of storage elements, for example, the first capacitor 121 to the third capacitor 123, may be electrically connected or disconnected to or from the light receiving element 110 via the switching unit 130, for example, a first switch 131 to a third switch 133. Selection of the first switch 131 to the third switch 133, in other words, selection of the first capacitor 121 to the third capacitor 123, is performed according to a control instruction of the controller 400, which is described below.

The first capacitor 121, as illustrated in FIG. 6, is connected to a first amplifier 121*a* that amplifies an electric signal stored in the first capacitor 121, i.e., a first electric signal. The first amplifier 121*a* is connected to a fourth switch 121*b* that is in turn connected to an output bus.

The second capacitor 122 and the third capacitor 123 are respectively connected to a second amplifier 122*a* and a third amplifier 123*a*, and the second amplifier 122*a* and the third amplifier 123*a* are in turn respectively connected to a fifth switch 122*b* and a sixth switch 123*b*.

The first to third switches 131 to 133, the first to third capacitors 121 to 123, the first to third amplifiers 121*a* to 123*a*, and the fourth to sixth switches 121*b* to 123*b* in FIG. 6 may be arranged in the CMOS chip 110*b* shown in FIGS. 3-5. In this case, the first to third switches 131 to 133 may correspond to a plurality of the transistor 110*d* shown in FIGS. 4 and 5, and the first to third capacitors 121 to 123 may correspond to the capacitor module 120 shown in FIGS. 4 and 5.

A process of storing the first to third electric signals in the storage elements, i.e., the capacitors 121 to 123, and acquiring first to third X-ray images from the first to third electric signals by the image processor 200 is described in detail below.

When or before the X-ray generator 10 emits first X-rays having a predetermined energy level, any one of the first to third switches 131 to 133, for example, the first switch 131, is selected according to a control instruction of the controller 400. Then, only the first capacitor 121 connected to the selected first switch 131 is connected to the light receiving element 110, and the second and third capacitors 122 and 123 connected to the other switches 132 and 133 are electrically disconnected from the light receiving element 110. In other words, the first storage element, i.e., the first capacitor 121, is selected.

When the light receiving element 110 converts first X-rays into an electric signal and outputs the electric signal, the capacitor electrically connected to the light receiving element 110 via the first switch 131 selected as described above, for example, the first capacitor 121, stores a first electric signal corresponding to the first X-rays.

Next, if X-ray imaging is performed using second X-rays having a different energy level than the first X-rays, another switch that has not been selected by the controller 400, for example, the second switch 132, is selected to electrically connect the second capacitor 122 to the light receiving element 110. The selection of the second switch 132 may be performed when or before the X-ray generator 10 emits the second X-rays to the subject. The second capacitor 122 then stores a second electric signal corresponding to the second X-rays.

Next, if X-ray imaging is performed using third X-rays having a different energy level than the first X-rays and the second X-rays, the third capacitor 123 is selected via the third switch 133 and stores a third electric signal corresponding to the third X-rays.

After the X-ray imaging has been completed, the fourth switch 121*b* electrically connected to the first capacitor 121 is closed to connect the first capacitor 121 to the output bus, and the first electric signal of the first capacitor 121 is transmitted to the image processor 200 through the output bus. The first electric signal stored in the first capacitor 121 is amplified by the first amplifier 121*a* for image processing. Thus, the image processor 200 generates a first X-ray image using the first electric signal and stores the first X-ray image in the storage unit 210.

Subsequently, after generation and storage of the first X-ray image by the image processor 200 are completed, the fifth switch 122*b* electrically connected to the second capacitor 122 is closed to connect the second capacitor 122 to the output bus, and the second electric signal of the second capacitor 122 is transmitted to the image processor 200 through the output bus. The image processor 200 generates a second X-ray image based on the second electric signal. The second amplifier 122*a* amplifies the second electric signal.

Next, after generation and storage of the second X-ray image by the image processor 200 are completed, the sixth switch 123*b* electrically connected to the third capacitor 123 is closed to connect the third capacitor 123 to the output bus, and the third electric signal of the third capacitor 123 is transmitted to the image processor 200 through the output bus. The image processor 200 generates a third X-ray image based on the third electric signal. The third amplifier 123a amplifies the third electric signal.

Through the above-described process, the image processor 200 may sequentially acquire the first to third X-ray images according to the first to third electric signals stored in the plurality of storage elements, i.e., the first to third capacitors 121 to 123.

The x-ray images read out by the image processor 200 are stored in the storage unit 210.

As necessary, the image processor 200 may retrieve an x-ray image stored in the storage unit 210, and perform predetermined image processing, for example, hue adjustment, sharpening, etc., on the x-ray image. In addition, the image processor 200 may retrieve a plurality of x-ray images stored in the storage unit 210, and overlap and combine the x-ray images, thereby generating, for example, a multi-energy X-ray (MEX) image or stereoscopic image. The MEX image or stereoscopic image may be temporarily or semi-permanently stored in the storage unit 210.

The X-ray image stored in the storage unit 210 may be displayed to the user, for example, a doctor or a patient, via the display unit 300 that displays the X-ray image. The display unit 300 may be provided in the X-ray imaging apparatus, or may be provided in an external terminal that is connected to the X-ray imaging apparatus via a wired or wireless network.

In the example illustrated in FIGS. 2 and 3, the controller 400 may be provided to control the X-ray generator 10 and the display unit 300, for example.

The controller 400 controls the above-described constituent elements. In particular, the controller 400 generates a control instruction to select only one storage element or a plurality of storage elements 121 to 123 of the storage element module 120 provided in each light receiving module 100 according to the energy level of X-rays emitted from the X-ray generator 10, thereby controlling the switching unit 130 (for example, individually controlling opening and closing of the first to third switches 131 to 133 as illustrated in FIG. 6). In this way, the controller 400 may allow only one of the plurality of storage elements 121 to 123 (for example, the first storage element 121) to store an electric signal corresponding to the received X-rays.

The controller 400, as illustrated in FIG. 3, may transmit the same control instruction to all of the switching units 130 (for example, transistors 110d) connected to the photodiodes 110c of the light receiving elements 110, thereby controlling selection of only the first storage elements 121 corresponding to the first X-rays of the storage elements 121 to 123 of the storage element module 120, such as a capacitor module.

In particular, in the case of imaging using first X-rays, if a capacitor selected from any one capacitor module 120 is the first capacitor 121, but a capacitor selected from another capacitor module 120 is the second capacitor 122, and the image processor 200 reads out a single X-ray image only from the first capacitors 121, the generated X-ray image may be unclear due to combination of the electric signals acquired from different X-rays. Accordingly, the same control instruction to select any one storage element 121, 122, or 123 from the storage element module 120 may be applied to all of the switching units 130.

An X-ray image generation method is described below with reference to FIGS. 7 to 11.

The X-ray image generation method includes determining an X-ray energy level to be emitted, selecting at least one capacitor from a plurality of capacitors of a capacitor module according to the determined X-ray energy level, emitting X-rays from an X-ray generator to a subject, receiving X-rays that have passed through the subject by light receiving elements of light receiving elements constituting an X-ray detection panel, converting the received X-rays into an electric signal, and outputting the electric signal, storing the output electric signal in the selected at least one capacitor, and generating an image by reading out the electric signal stored in the selected capacitor.

Figure 7:
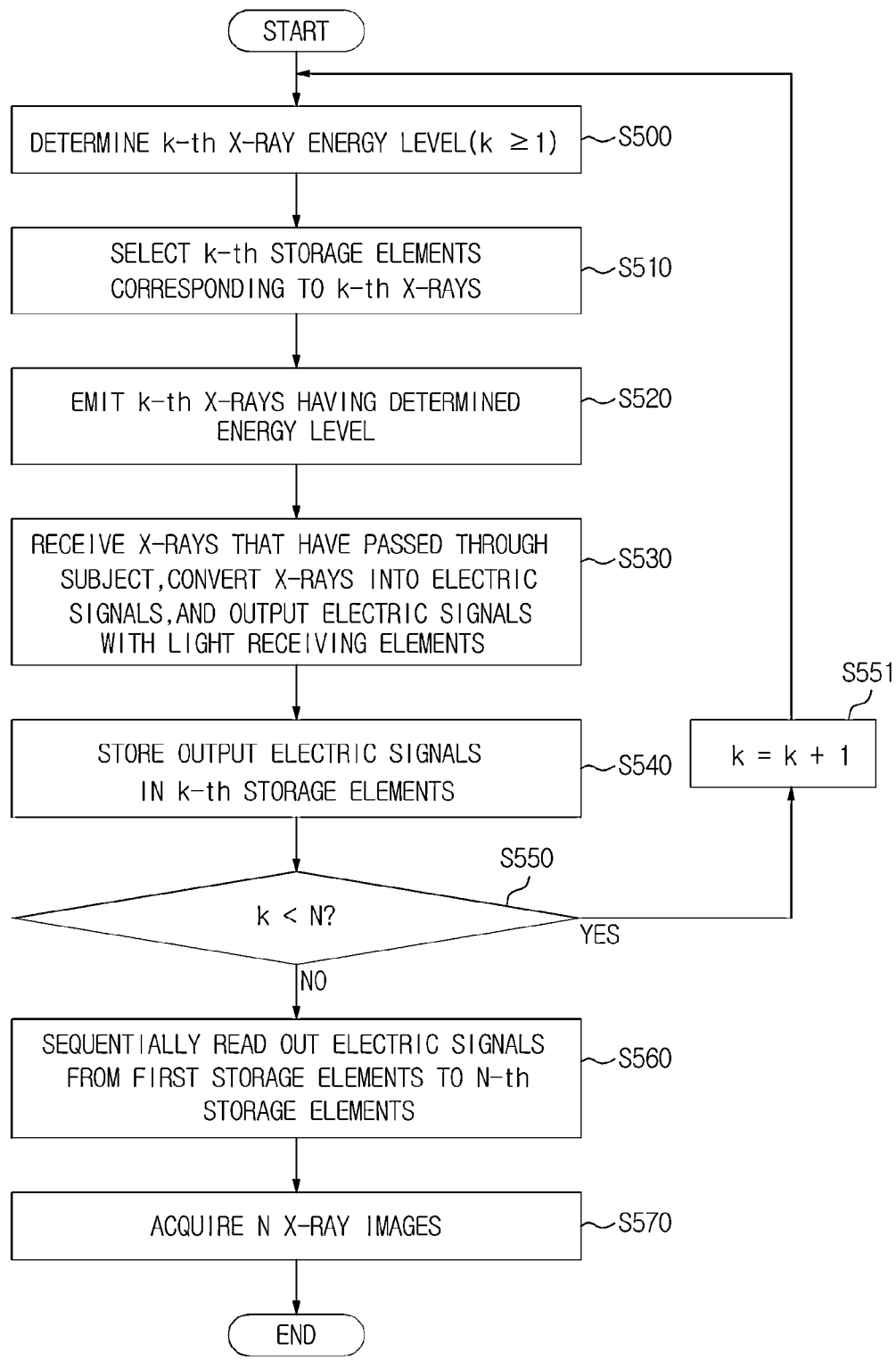
FIG. 7 is a flowchart illustrating an example of an X-ray image generation method.

FIG. 7 is a flowchart illustrating an example of the X-ray image generation method. Assuming that a total of N X-ray images are acquired by emitting X-rays N times, first, an energy level of k-th X-rays ($k \geq 1$) to be emitted is determined according to a user selection or preset conditions (S500).

Then, the controller 400 selects k-th storage elements (for example, the first storage elements 121) corresponding to the k-th X-rays of the plurality of storage elements 121 to 123 within the plurality of storage element modules 120 according to the determined X-ray energy level, and transmits a control instruction based on the selection result to the switching units 130 to electrically connect the light receiving elements 110 to the k-th storage elements 121 (S510).

Thereafter, the X-ray generator 10 of the X-ray imaging apparatus emits the k-th X-rays to a subject (S520).

The k-th X-rays may pass through the subject or may be directly transmitted to the X-ray detection panel 20. The light receiving elements 10 of the X-ray detection panel 20 receive the k-th X-rays. The scintillators 110a of the light receiving elements 110 flash in response to the received X-rays, in other words, output visible photons. The photodiodes 110c receive the output visible photons, convert the visible photons into electric signals, and output the electric signals (S530).

The k-th storage elements 121 that are electrically connected to the light receiving elements 110 by the switching units 130 as described above store the output electric signals (S540).

Thereafter, if the number of X-ray emission operations or the number of the storage elements in which the electric signals are stored is less than a desired number N of X-ray images (S550), k is increased by 1 and the aforementioned operations are repeated (S551). Of course, X-ray imaging may be additionally performed according to user settings.

The image processor 200, as described above with reference to FIGS. 2, 3, and 6, sequentially reads out the first to N-th electric signals stored in the first to N-th storage elements (S560), thereby acquiring first to N-th X-ray images (S570).

The process of emitting X-rays a plurality of times and storing a plurality of electric signals corresponding to the emitted X-rays is described in greater detail below with reference to FIGS. 8 and 9.

Figure 8:
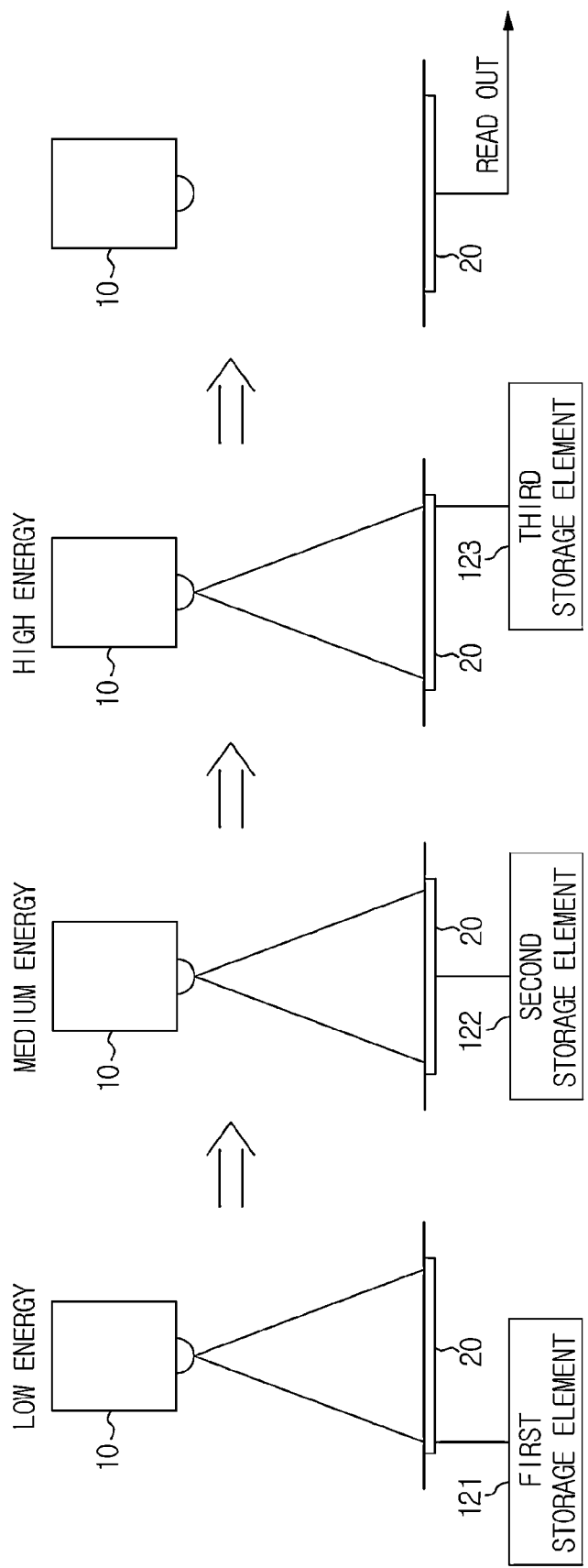
FIG. 8 is a diagram illustrating an example of emitting X-rays a plurality of times from an X-ray generator in the X-ray image generation method.
Figure 9:
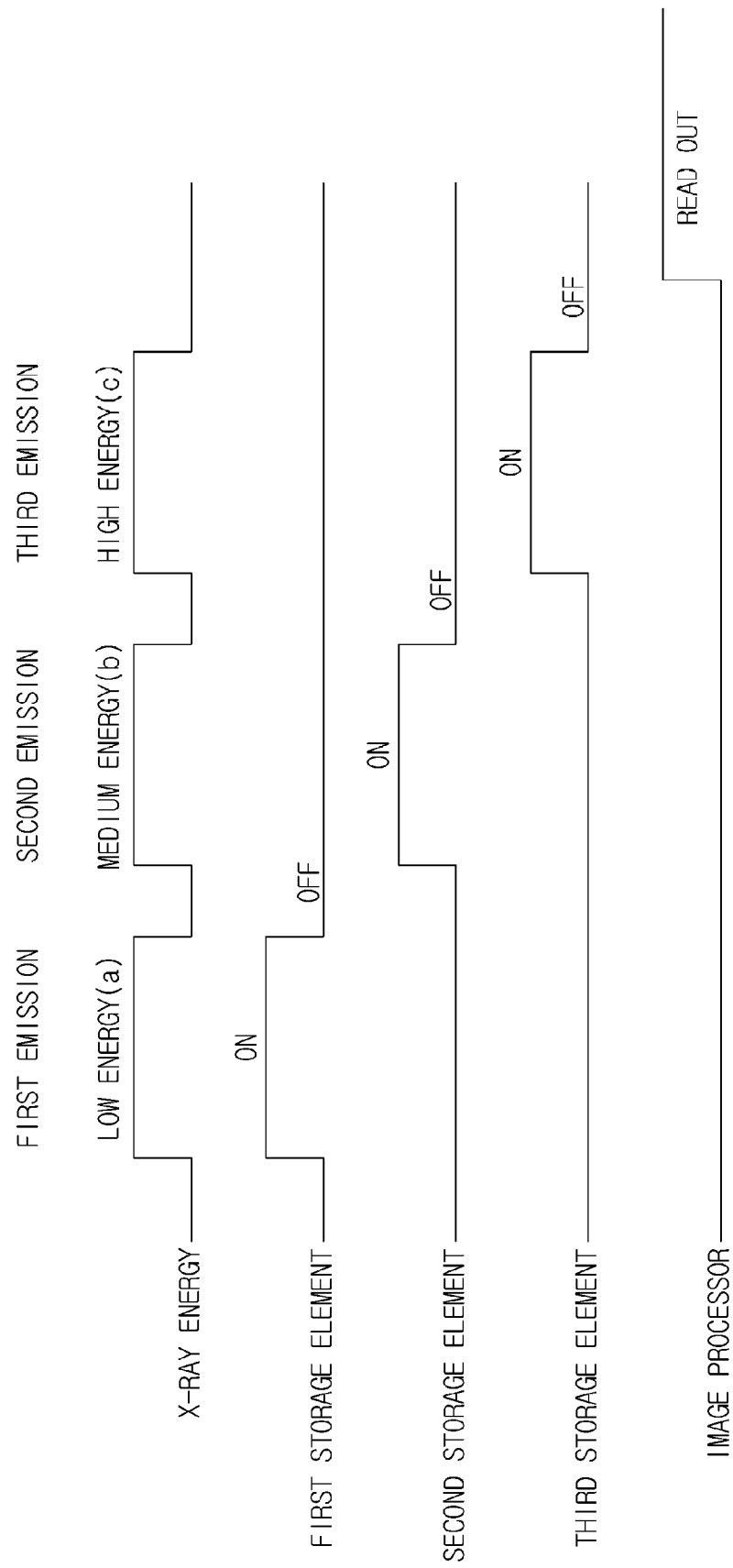
FIG. 9 is a diagram illustrating an example of X-ray energy levels and operation of a plurality of storage elements in the X-ray image generation method.

FIG. 8 is a diagram illustrating an example of emitting X-rays a plurality of times from the X-ray generator 10 in the X-ray image generation method, and FIG. 9 is a diagram illustrating an example of X-ray energy levels and operation of a plurality of storage elements 121, 122, 123 in the X-ray image generation method.

As illustrated in FIGS. 8 and 9, first, a low X-ray energy level to be emitted is selected (S500).

A storage element allotted to the low X-ray energy level, for example, the first storage element 121, is selected (S510), and is electrically connected to the light receiving element 110 of the X-ray detection panel 20 to be used to store an electric signal from the light receiving element 110.

That is, it can be said that the first storage element 121 is activated for detection of first X-rays. As illustrated in FIG. 9, a connection between the first storage element 121 and the light receiving element 110 via the first switch 131 is represented by an on state of the first storage element 121.

Thereafter, if the X-ray generator 10 emits first X-rays having a low energy level ((a) of FIG. 9) toward the X-ray detection panel 20, a first electric signal acquired from the first X-rays having the low energy level is stored in the first storage element 121 through the above-described operations S520 to S540. After storing the first electric signal, as illustrated in FIG. 9, the first storage element 121 is switched off. In other words, the first switch 131 is opened to electrically disconnect the first storage element 121 from the light receiving element 110. Even after being electrically disconnected from the light receiving element 110, the first storage element 121 retains the stored first electric signal.

Upon emission of second X-rays, a medium energy level greater than the low energy level ((b) of FIG. 9) is selected as an energy level of second X-rays to be emitted (S500). Next, a storage element for storage of X-rays having the medium energy level, for example, the second storage element 122, is selected according to a control instruction output from the controller 400 and is electrically connected to the light receiving element 110 of the X-ray detection panel 20 (S510). The X-ray generator 10 emits the X-rays having the medium energy level, and a second electric signal corresponding to the X-rays having the medium energy level is stored in the second storage element 122 through the above-described operations S520 to S540. In other words, when the second X-rays are emitted as illustrated in FIG. 9, i.e., when the second emission of X-rays is initiated, the second storage element 122 is switched on. As in the case of the first storage element 121, after storing the second electric signal, the second storage element 122 is electrically disconnected from the light receiving element 110 and is switched off.

Subsequently, a high energy level of third X-rays to be emitted is selected (S500). When the third X-rays are emitted, the third storage element 123 is activated, i.e., is switched on, to store a third electric signal corresponding to the third X-rays (S520 to S540).

By repeating the above-described operations, first to N-th electric signals respectively corresponding respectively to first to N-th X-rays that are emitted a total of N times are stored in first to N-th storage elements.

The image processor 200, as described above with reference to FIGS. 2, 3, and 6, sequentially reads out the first to N-th electric signals stored in the first to N-th storage elements (S560), thereby acquiring first to N-th X-ray images (S570).

For convenience of illustration, FIG. 8 shows the first to third storage elements 121 to 123 as being separate from the X-ray detection panel 20. However, the first to third storage elements 121 to 123 may be included in the X-ray detection panel 20 as shown, for example, in FIG. 2.

Figure 10:
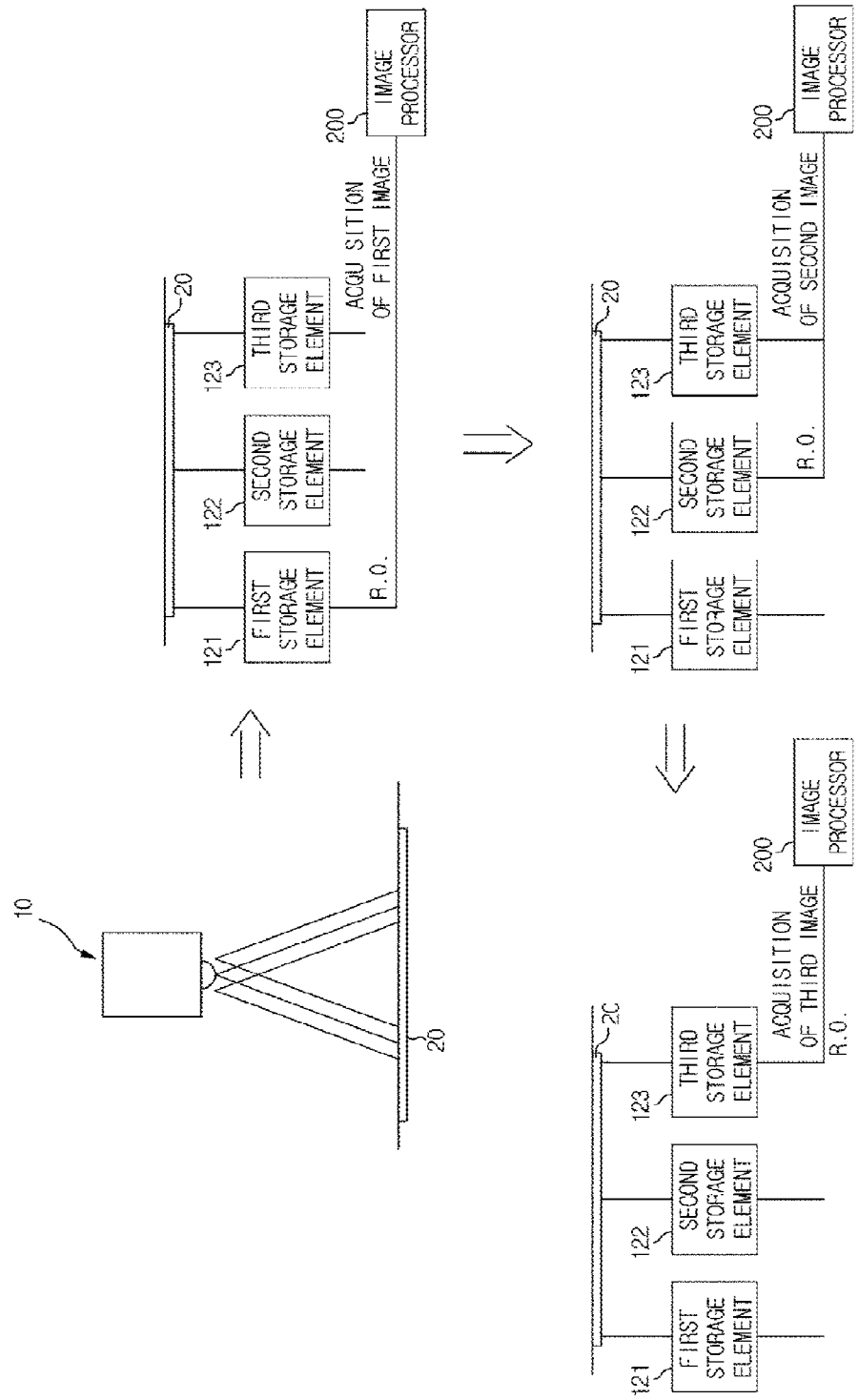
FIG. 10 is a diagram illustrating an example of reading out X-ray images a plurality of times from an X-ray detection panel in the X-ray image generation method.

The image processor 200 begins to operate only after the respective storage elements 121 to 123 have stored electric signals, i.e., the first to third electric signals as illustrated in FIG. 9. The image processor 200 may acquire first to third X-ray images by sequentially reading out the first to third electric signals as illustrated in FIG. 10. The image processor 200 may be controlled by a control instruction of the controller 400 as described above.

The operation of the image processor 200 is described in greater detail below with reference to FIG. 10.

FIG. 10 is a diagram illustrating an example of reading out X-ray images a plurality of times from an X-ray detection panel 20 in the X-ray image generation method. In this example, X-rays are successively emitted three times, and the storage elements 121 to 123 respectively store first to third electric signals.

Then, as illustrated in FIG. 10, the first storage element 121 storing the first electric signal is connected to an output bus, and the image processor 200 generates a first X-ray image using the first electric signal transmitted through the output bus. Next, the second storage element 122 storing the second electric signal is connected to the output bus, and the image processor 200 generates a second X-ray image using the second electric signal transmitted through the output bus. Finally, the third storage element 123 storing the third electric signal is connected to the output bus, and the image processor 200 generates a third X-ray image using the third electric signal transmitted through the output bus. As a result, the first X-ray image to the third X-ray image are acquired.

Through the above-described method, the image processor 200 sequentially reads out the first to third X-ray images from the first to third storage elements 121 to 123.

One example of image acquisition via the above-described image processor 200 and the output bus has been described above with reference to FIG. 7.

The above description has explained the method of successively emitting various energy levels of X-rays to the same subject, and acquiring X-ray images respectively corresponding to the X-rays having the various energy levels after the X-ray emission is completed.

Figure 11:
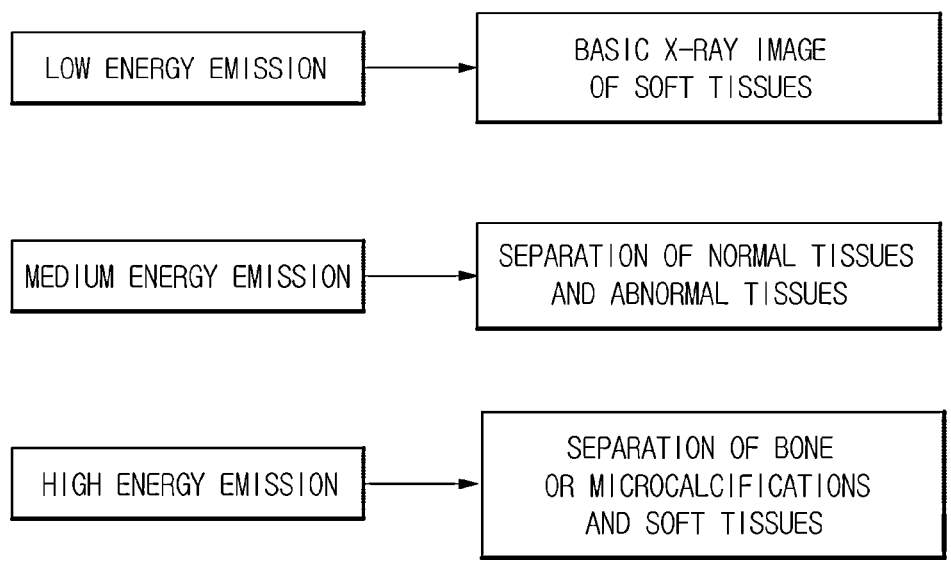
FIG. 11 is a diagram illustrating an example of images acquired according to X-ray energy levels in the X-ray image generation method.

By successively emitting X-rays having various energy levels, for example, X-rays having a low energy level, a medium energy level, and a high energy level to the same subject for X-ray imaging, different X-ray images corresponding to the various energy levels of the X-rays may be acquired as illustrated in FIG. 11, which enables detection of various tissues inside the subject.

This is because various tissues inside the subject may have different X-ray absorption or transmittance according to the X-ray energy level emitted from the X-ray generator 10. For example, if X-rays having a high energy level are emitted to a human body, soft tissues transmit X-rays, but tissues such as bones absorb X-rays. Thus, upon emission of X-rays having the high energy level, an image of hard tissues, such as bones, excluding soft tissues may be acquired. Conversely, when X-rays having a low energy level are emitted to a human body, an image of soft tissues may be acquired. Accordingly, it may be necessary to emit X-rays having various energy levels to obtain images of different tissues of a subject.

For convenience of illustration, FIG. 10 shows the first to third storage elements 121 to 123 as being separate from the X-ray detection panel 20. However, the first to third storage elements 121 to 123 may be included in the X-ray detection panel 20 as shown, for example, in FIG. 2.

FIG. 11 is a diagram illustrating an example of images acquired according to X-ray energy levels in the X-ray image generation method. As illustrated in FIG. 11, if X-rays having a low energy level are emitted to the subject, a basic X-ray image of soft tissues may be acquired. If X-rays having a medium energy level greater than the low energy level are emitted to the subject, X-ray images separating normal tissues and abnormal tissues may be acquired. If X-rays having a high energy level greater than the medium energy level are emitted to the subject, X-ray images separating bone or microcalcifications and soft tissues may be acquired.

Accordingly, if X-rays having different energy levels are emitted to the same subject, different X-ray images of the same subject may be acquired, which ensures a more accurate diagnosis of tissues or structures inside a human body or an object. In addition, a multi-energy X-ray image or a stereoscopic image may be acquired by combining X-ray images acquired from X-rays having different energy levels.

An example of a Full Field Digital Mammography (FFDM) apparatus is described below with reference to FIGS. 12 and 13.

Figure 12:
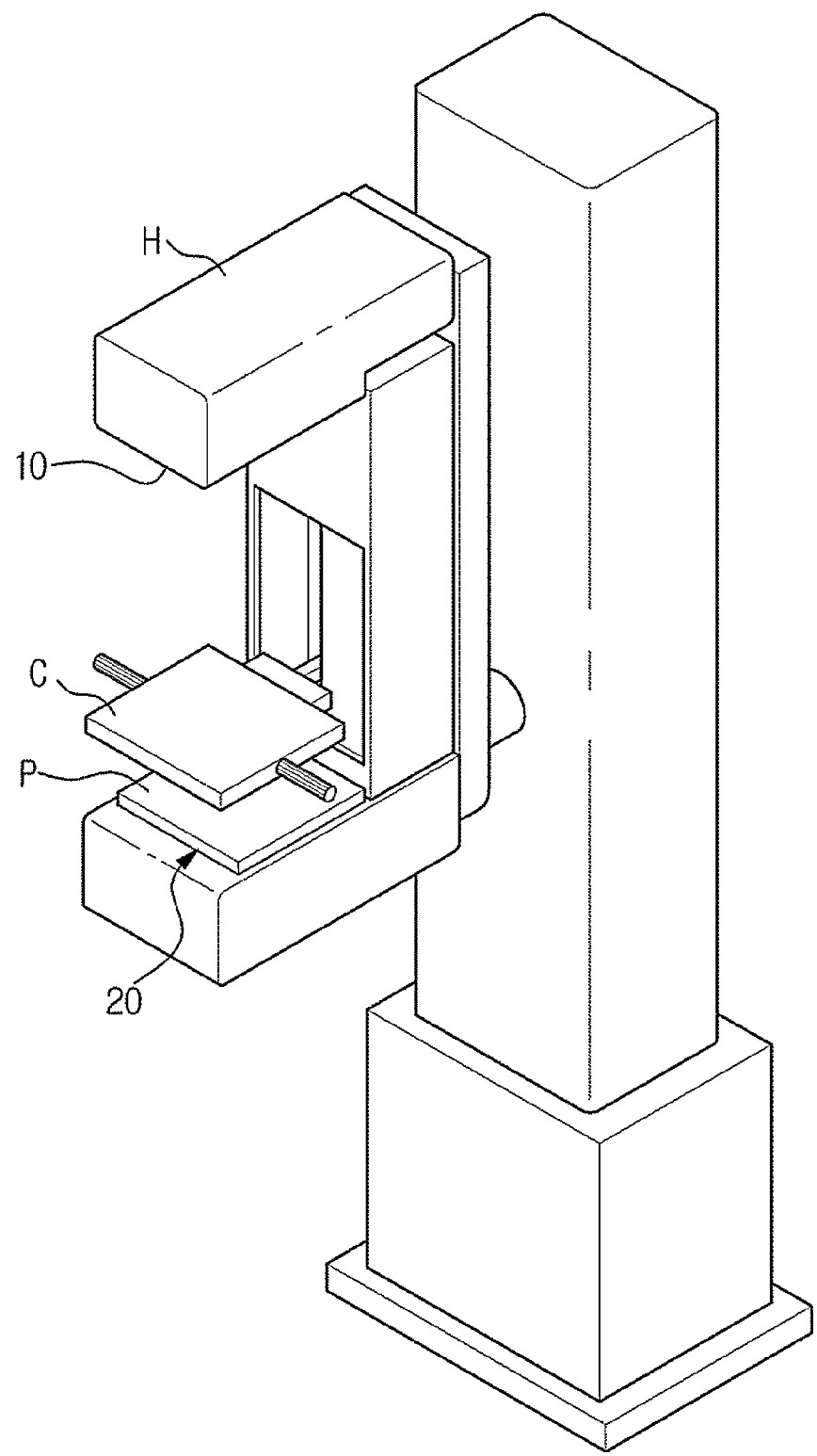
FIG. 12 is a perspective diagram illustrating an example of a Full Field Digital Mammography (FFDM) apparatus.

FIG. 12 is a perspective diagram illustrating an example of an FFDM apparatus. As illustrated in FIG. 12, the FFDM apparatus includes an upper member H including the X-ray generator 10 to generate and emit X-rays to the subject, i.e., a breast, and a support member P on which the breast is placed. The support member P includes the X-ray detection panel 20 to detect X-rays that have passed through the subject. In addition, in the case of the FFDM apparatus, a compressor C to compress the breast is located between the upper member H and the support member P.

The X-ray generator 10 of the FFDM apparatus may emit X-rays having various energy levels. However, in the case of the FFDM apparatus, since the breast is mainly formed of soft tissues, X-rays having a low energy level may be emitted to acquire an X-ray image to reduce radiation exposure.

However, various images of the breast may be acquired by emitting X-rays having different energy levels in a plurality of emissions, which ensures a more accurate diagnosis of diseases of the breast, for example, breast cancer tissues, using X-ray imaging.

In one example of the FFDM apparatus, the X-ray detection panel 20, as illustrated in FIGS. 2 and 3, consists of the plurality of light receiving modules 100, and each of the light receiving modules 100 includes the light receiving element 110 including the scintillator 110a and the CMOS chip 110b, and the capacitor module 120 including the plurality of capacitors 121 to 123 that can be electrically connected to or disconnected from the light receiving element 110.

A method of acquiring an X-ray image using the FFDM apparatus is described below.

Figure 13:
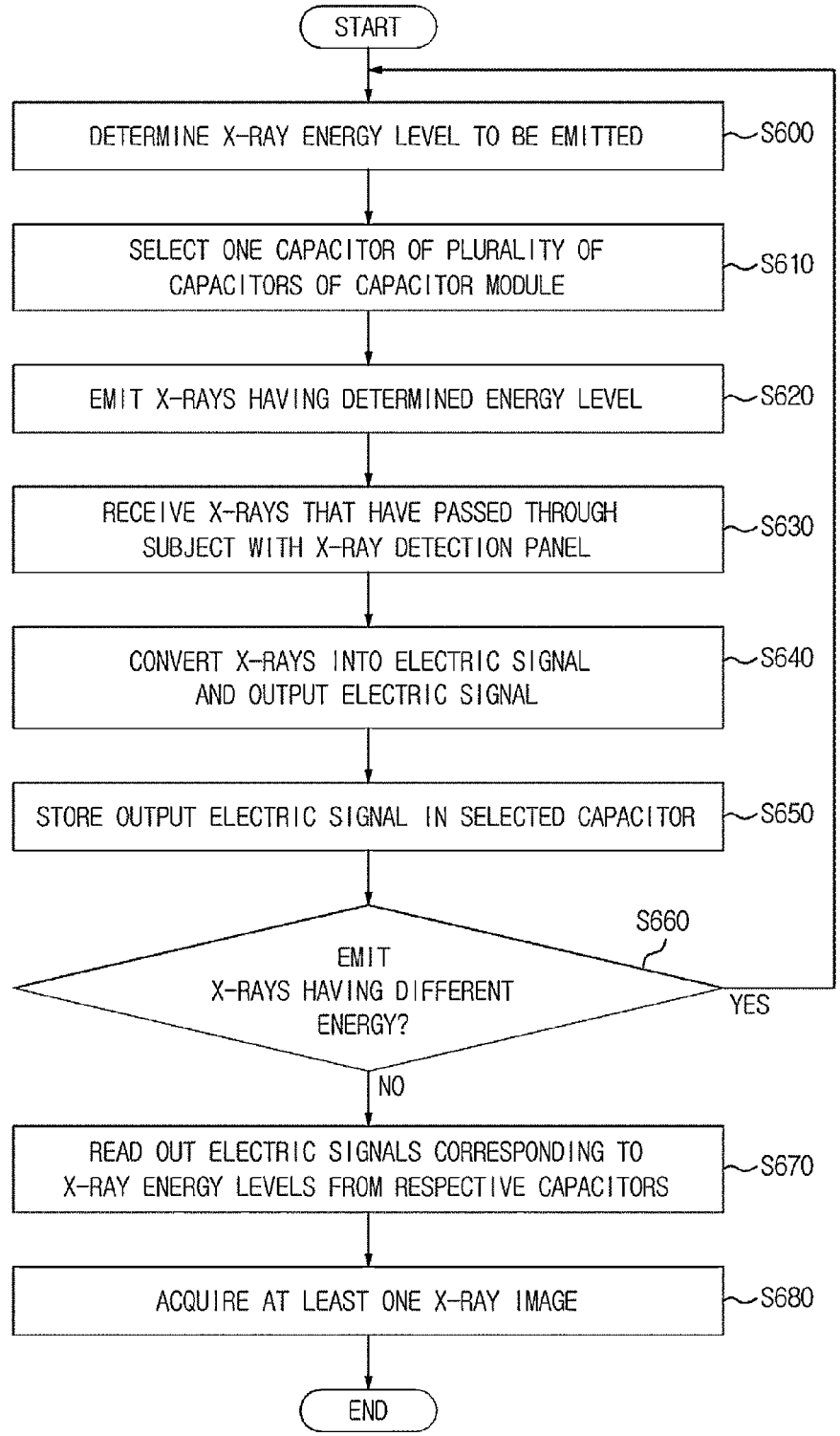
FIG. 13 is a flowchart illustrating an example of a method of acquiring an X-ray image using the FFDM apparatus.

FIG. 13 is a flowchart illustrating an example of a method of acquiring an X-ray image using the FFDM apparatus. As illustrated in FIG. 13, to acquire an X-ray image using the FFDM apparatus, first, an X-ray energy level to be emitted is determined according to a user selection or preset conditions of the FFDM apparatus (S600).

Any one capacitor (for example, the first capacitor 121) of the plurality of capacitors 121, 122, 123 of the capacitor module 120 is selected according to the determined X-ray energy level, and any one switch (for example, the first switch 131) connected to the selected capacitor is closed to connect the selected first capacitor 121 to the light receiving element 110 (S610). In this case, the other capacitors (for example, the capacitors 122 and 123) are electrically disconnected from the light receiving element 110.

Then, X-rays having the energy level determined in operation S600 are emitted (S620).

The light receiving element 110 of the X-ray detection panel 20 receives X-rays that have passed through the subject, i.e., a breast (operation S630), converts the X-rays into an electric signal, and outputs the electric signal (S640).

The selected first capacitor 121 stores the output electric signal (S650).

Thereafter, whether or not to emit X-rays having a different energy level is determined according to a user selection or preset conditions of the FFDM apparatus (S660).

When X-rays having a different energy level are to be emitted, the above operations S600 to S650 are repeated.

When X-rays having a different energy level are not to be emitted, that is, when X-ray imaging of the subject, i.e., a breast, using all desired energy levels has been completed, an image processor of the FFDM apparatus reads out electric signals corresponding to the X-ray energy levels from respective ones of the capacitors 121 to 123 (S670). As a result, at least one X-ray image of the breast is acquired (S680).

As is apparent from the above description, the X-ray detection panel 20, the X-ray image generation method using the X-ray detection panel 20, and the X-ray imaging apparatus using the X-ray detection panel 20 described above enable easy and rapid acquisition of a plurality of X-ray images corresponding to multiple energy levels of X-rays when generating a multi-energy X-ray image.

The image processor 200 illustrated in FIGS. 2, 3, 6, and 10 and the controller 400 illustrated in FIGS. 2 and 3 that perform the operations illustrated in FIGS. 7-11 and 13 may be implemented using one or more hardware components, one or more software components, or a combination of one or more hardware components and one or more software components.

A hardware component may be, for example, a physical device that physically performs one or more operations, but is not limited thereto. Examples of hardware components include resistors, capacitors, inductors, power supplies, frequency generators, operational amplifiers, power amplifiers, low-pass filters, high-pass filters, band-pass filters, analog-to-digital converters, digital-to-analog converters, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may have various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Software or instructions for controlling a processing device to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments for implementing the examples disclosed herein can be easily constructed by a programmer skilled in the art to which the examples pertain based on the drawings and their corresponding descriptions as provided herein.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An X-ray imaging apparatus comprising:
   an X-ray generator configured to emit X-rays to a subject in a plurality of times;
   an X-ray detection panel comprising:
      light receiving elements, each light receiving element configured to receive X-rays that have passed through the subject, convert the X-rays into electric signals, and output the electric signals corresponding to the X-rays emitted in a plurality of times; and
      capacitor modules, each respective capacitor module being connected to a respective light receiving element, each capacitor module comprising capacitors connected to a corresponding light receiving element of the light receiving elements and configured to store the electric signals output from the corresponding light receiving element in each capacitor of the capacitors sequentially; and
   an image processor configured to read out the electric signals stored in each capacitor of each capacitor module of the capacitor modules sequentially after emission of the X-rays in a plurality of times is completed, and to generate X-ray images, wherein
   the X-ray generator emits X-rays having successively increasing energy levels comprising first X-rays having a low energy level that acquire a basic X-ray image of soft tissues, second X-rays having a medium energy level that separate normal tissues and abnormal tissues in response to the first X-rays, and third X-rays having a high energy level that acquire bones excluding soft tissues in response to the second X-rays.

2. The X-ray imaging apparatus of claim 1, wherein one of the capacitors is further configured to be electrically connected to or disconnected from the corresponding light receiving element according to an X-ray energy level of the X-rays emitted from the X-ray generator, and store the electric signal output from the corresponding light receiving element in response to the corresponding light receiving element receiving X-rays while the one of the capacitors is electrically connected to the corresponding light receiving element.

3. The X-ray imaging apparatus of claim 1, further comprising:
   switching units respectively corresponding to the light receiving elements, each switching unit of the switching units being configured to select the one of the capacitors connected to the corresponding light receiving element according to an X-ray energy level of the X-rays emitted from the X-ray generator to enable the selected one of the capacitors to store the electric signal output from the corresponding light receiving element.

4. The X-ray imaging apparatus of claim 3, wherein each switching unit of the switching units is further configured to select capacitors of the capacitor modules connected to the corresponding light receiving element according to X-ray energy levels of the X-rays emitted from the X-ray generator to enable the selected capacitors to respectively store electric signals respectively corresponding to the X-ray energy levels output from the corresponding light receiving element; and the image processor is further configured to read out the electric signals respectively corresponding to the X-ray energy levels stored in the selected capacitors of the capacitor modules according to the X-ray energy levels to generate X-ray images respectively corresponding to the X-ray energy levels.

5. The X-ray imaging apparatus of claim 1, wherein the X-ray generator is further configured to emit X-rays having X-ray energy levels to the subject by emitting the X-rays to the subject with a different X-ray energy level each of times the X-rays are emitted to the subject;

each of the light receiving elements is further configured to output the electric signal in response to receiving the X-rays that have passed through the subject; and the capacitors of each of the capacitor modules are further configured to store the electric signal output from the corresponding light receiving element in a different one of the capacitors according to an X-ray energy level of the X-rays emitted to the subject each of the times the X-rays are emitted to the subject.

6. The X-ray imaging apparatus of claim 5, wherein the image processor is further configured to read out electric signals corresponding to a same X-ray energy level from the capacitors of the capacitor modules.

7. The X-ray imaging apparatus of claim 1, wherein each of the light receiving elements comprises:

a scintillator configured to receive the X-rays that have passed through the subject, and generate light in response to the X-rays; and a photodiode configured to sense the light generated by the scintillator, and output the electric signal in response to the light.

8. The X-ray imaging apparatus of claim 7, wherein the X-ray detection panel further comprises:

a wafer comprising the light receiving elements; and a wiring layer comprising the capacitor modules; and the X-ray detection panel is a front-side illumination type X-ray detection panel in which the wiring layer is disposed between the scintillator and the wafer, and the X-ray detection panel is configured to receive the X-rays that have passed through the subject on a surface of the scintillator facing away from the wiring layer; or the X-ray detection panel is a back-side illumination type X-ray detection panel in which the wafer is disposed between the scintillator and the wiring layer, and the X-ray detection panel is configured to receive the X-rays that have passed through the subject on a surface of the scintillator facing away from the wafer.

9. The X-ray imaging apparatus of claim 1, further comprising: a controller configured to select capacitors to store x-rays having the successively increasing energy levels.

10. An X-ray image generation method comprising:

selecting, for each capacitor module of capacitor modules comprising capacitors, respectively, a capacitor among the capacitors according to an X-ray energy level of X-rays to be emitted from an X-ray generator;

emitting X-rays having successively increasing energy levels from the X-ray generator to a subject in a plurality of times, comprising first X-rays having a low energy level that acquire a basic X-ray image of soft tissues, second X-rays having a medium energy level that separate normal tissues and abnormal tissues in response to the first X-rays, and third X-rays having a high energy level that acquire bones excluding soft tissues in response to the second X-rays;

receiving X-rays that have passed through the subject with each light receiving element of light receiving elements respectively corresponding to a capacitor module of the capacitor modules, each light receiving element of the light receiving elements converting the X-rays to electric signals and outputting the electric signals corresponding to the X-rays emitted in a plurality of times to the capacitor module corresponding to the light receiving element;

storing, by the capacitor selected among the capacitors, the electric signal from the corresponding light receiving element in each capacitor of the capacitors sequentially;

reading out the electric signals stored in each capacitor of each capacitor module of the capacitor modules sequentially after emission of the X-rays in a plurality of times is completed; and generating X-ray images based on the electric signals.

11. The X-ray image generation method of claim 10, further comprising:

reading out the electric signal stored in the capacitor of each capacitor module of the capacitor modules to generate an X-ray image.

12. The X-ray image generation method of claim 10, further comprising:

repeating the selecting, the emitting, the receiving, and the storing for each of different X-ray energy levels of the X-rays to be emitted from the X-ray generator to store different electric signals respectively corresponding to the different X-ray energy levels in the capacitors of each capacitor module of the capacitor modules.

13. The X-ray image generation method of claim 12, further comprising:

reading out the stored different electric signals respectively corresponding to the different X-ray energy levels to generate X-ray images respectively corresponding to the different X-ray energy levels.

14. An X-ray detection panel comprising:

a light receiving element configured to receive X-rays in a plurality of times, and output electric signals corresponding to the X-rays received in a plurality of times; and storage elements connected to the light receiving element, each respective storage element configured to selectively store the electric signals output from the light receiving element sequentially, wherein the storage elements are further configured to output the electric signals sequentially after a receiving of the X-rays in the plurality of times is completed, wherein the light receiving element is configured to receive X-rays having successively increasing energy levels, comprising first X-rays having a low energy level that acquire a basic X-ray image of soft tissues, second X-rays having a medium energy level that separate normal tissues and abnormal tissues in response to the first X-rays, and third X-rays having a high energy level that acquire bones excluding soft tissues in response to the second X-rays.

15. The X-ray detection panel of claim 14, wherein one of the storage elements is further configured to be electrically connected to or disconnected from the light receiving element depending on an X-ray energy level, and store the electric signal output from the light receiving element in response to the light receiving element receiving X-rays while the one of the storage elements is electrically connected to the light receiving element.

16. The X-ray detection panel of claim 14, further comprising a switching unit configured to select any one storage element of the storage elements connected to the light receiving element according to an X-ray energy level, and electrically connect the selected storage element to the light receiving element to enable the selected storage element to store the electric signal output from the light receiving element so that the stored electric signal corresponds to the X-ray energy level.

17. The X-ray detection panel of claim 14, the storage elements are further configured to selectively store the electric signal output from the light receiving element in a different one of the storage elements each of times the light receiving element receives X-rays.

18. The X-ray detection panel of claim 14, wherein the X-ray detection panel is configured to read out the electric signals stored in the storage elements to generate X-ray images in response to the light receiving element receiving the X-rays.

19. The X-ray detection panel of claim 18, wherein the X-rays received by the light receiving element respectively correspond to different X-ray energy levels, wherein each storage element is configured to store electric signals corresponding to the different X-ray energy levels.

20. The X-ray detection panel of claim 14, wherein the light receiving element comprises:
   a scintillator configured to receive the X-rays, and generate light in response to the X-rays; and
   a complementary metal-oxide-semiconductor (CMOS) chip comprising a photodiode configured to sense the light generated by the scintillator, and output an electric signal in response to the light generated by the scintillator.

21. The X-ray detection panel of claim 20, further comprising:
   a wiring layer comprising the storage elements;
   wherein the X-ray detection panel is a back-side illumination type X-ray detection panel in which the CMOS chip is disposed between the scintillator and the wiring layer, and the X-ray detection panel is configured to receive the X-rays on a surface of the scintillator facing away from the CMOS chip.

22. The X-ray detection panel of claim 14, wherein each of the storage elements is configured to temporarily store an electric signal of the electric signals and delete the electric signal in response to a new X-ray imaging being performed.

* * * * *